US009226983B2

(12) United States Patent
Benatuil et al.

(10) Patent No.: US 9,226,983 B2
(45) Date of Patent: Jan. 5, 2016

(54) TNF-α BINDING PROTEINS

(75) Inventors: Lorenzo Benatuil, Northborough, MA (US); Tariq Ghayur, Holliston, MA (US); Carrie L. Goodreau, Ludlow, MA (US); Peter C. Isakson, Southborough, MA (US); Jochen Salfeld, Grafton, MA (US)

(73) Assignee: AbbVie Inc., North Chicago, IL (US)

( * ) Notice: Subject to any disclaimer, the term of this patent is extended or adjusted under 35 U.S.C. 154(b) by 216 days.

(21) Appl. No.: 13/081,212

(22) Filed: Apr. 6, 2011

(65) Prior Publication Data

US 2011/0250130 A1 Oct. 13, 2011

Related U.S. Application Data

(60) Provisional application No. 61/321,633, filed on Apr. 7, 2010.

(51) Int. Cl.
A61K 51/10 (2006.01)
A61K 47/48 (2006.01)
C07K 16/24 (2006.01)
G01N 33/68 (2006.01)
A61K 39/00 (2006.01)

(52) U.S. Cl.
CPC ....... *A61K 51/1021* (2013.01); *A61K 47/48546* (2013.01); *C07K 16/241* (2013.01); *G01N 33/6863* (2013.01); *A61K 2039/505* (2013.01); *C07K 2317/24* (2013.01); *C07K 2317/76* (2013.01); *C07K 2317/92* (2013.01); *G01N 2333/7151* (2013.01)

(58) Field of Classification Search
None
See application file for complete search history.

(56) References Cited

U.S. PATENT DOCUMENTS

| | | | |
|---|---|---|---|
| 5,225,539 A * | 7/1993 | Winter | 530/387.3 |
| 5,624,821 A | 4/1997 | Winter et al. | |
| 5,648,260 A | 7/1997 | Winter et al. | |
| 5,837,242 A * | 11/1998 | Holliger et al. | 424/136.1 |
| 6,090,382 A | 7/2000 | Salfeld et al. | |
| 6,180,370 B1 * | 1/2001 | Queen et al. | 435/69.6 |
| 6,258,562 B1 | 7/2001 | Salfeld et al. | |
| 6,509,015 B1 | 1/2003 | Salfeld et al. | |
| 6,696,620 B2 * | 2/2004 | Hiatt et al. | 506/17 |
| 7,186,820 B2 | 3/2007 | Athwal et al. | |
| 7,223,394 B2 | 5/2007 | Salfeld et al. | |
| 7,531,169 B2 * | 5/2009 | Singh et al. | 424/130.1 |
| 7,541,031 B2 | 6/2009 | Salfeld et al. | |
| 7,588,761 B2 | 9/2009 | Salfeld et al. | |
| 7,612,181 B2 | 11/2009 | Wu et al. | |
| 7,700,739 B2 * | 4/2010 | Lacy et al. | 530/387.1 |
| 8,197,813 B2 | 6/2012 | Salfeld et al. | |
| 8,206,714 B2 | 6/2012 | Salfeld et al. | |
| 8,372,400 B2 | 2/2013 | Salfeld et al. | |
| 8,372,401 B2 | 2/2013 | Salfeld et al. | |
| 8,414,894 B2 | 4/2013 | Salfeld et al. | |
| 2003/0206898 A1 * | 11/2003 | Fischkoff et al. | 424/130.1 |
| 2003/0219438 A1 | 11/2003 | Salfeld et al. | |
| 2005/0042664 A1 | 2/2005 | Wu et al. | |
| 2006/0024308 A1 | 2/2006 | Crea | |
| 2007/0003547 A1 | 1/2007 | Foote | |
| 2008/0247941 A1 | 10/2008 | Schubert et al. | |
| 2009/0028794 A1 | 1/2009 | Medich et al. | |
| 2009/0145813 A1 | 6/2009 | Kim et al. | |
| 2009/0148513 A1 * | 6/2009 | Fraunhofer et al. | 424/451 |
| 2009/0175847 A1 | 7/2009 | Barghorn et al. | |
| 2009/0202487 A1 * | 8/2009 | Chang et al. | 424/85.7 |
| 2009/0203037 A1 | 8/2009 | Brophy et al. | |
| 2009/0239259 A1 | 9/2009 | Hsieh | |
| 2009/0263382 A1 | 10/2009 | Ewert et al. | |
| 2009/0285830 A1 | 11/2009 | Adams et al. | |
| 2009/0311253 A1 | 12/2009 | Ghayur et al. | |
| 2010/0040537 A1 | 2/2010 | Gu et al. | |
| 2010/0076178 A1 | 3/2010 | Ghayur et al. | |
| 2010/0266531 A1 | 10/2010 | Hsieh et al. | |
| 2011/0250130 A1 | 10/2011 | Benatuil et al. | |
| 2012/0034160 A1 | 2/2012 | Ghayur et al. | |
| 2012/0230911 A1 | 9/2012 | Hsieh et al. | |
| 2012/0258114 A1 | 10/2012 | Salfeld et al. | |
| 2013/0115224 A1 | 5/2013 | Salfeld et al. | |
| 2013/0171096 A1 | 7/2013 | Hsieh et al. | |

FOREIGN PATENT DOCUMENTS

| | | |
|---|---|---|
| WO | 9211383 | 7/1992 |
| WO | 9729131 A1 | 8/1997 |
| WO | 2004050683 A2 | 6/2004 |
| WO | 2005014650 A1 | 2/2005 |
| WO | 2005035575 A2 | 4/2005 |
| WO | 2006119107 A2 | 11/2006 |

(Continued)

OTHER PUBLICATIONS

Möller et al. Monoclonal antibodies to human tumor necrosis factor alpha: in vitro and in vivo application. Cytokine. May 1990;2(3):162-9.*
Rudikoff et al. Single amino acid substitution altering antigen-binding specificity. Proc Natl Acad Sci U S A. Mar. 1982;79(6):1979-83.*
MacCallum et al. Antibody-antigen interactions: contact analysis and binding site topography. J Mol Biol. Oct. 11, 1996;262(5):732-45.*
De Pascalis et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*

(Continued)

*Primary Examiner* — David Romeo
(74) *Attorney, Agent, or Firm* — Lathrop & Gage LLP.; James H. Velema, Esq.

(57) ABSTRACT

Isolated binding proteins, e.g., antibodies or antigen binding portions thereof, which bind to tumor necrosis factor-alpha (TNF-α), e.g., human TNF-α, and related antibody-based compositions and molecules are disclosed. Also disclosed are pharmaceutical compositions comprising the antibodies, as well as therapeutic and diagnostic methods for using the antibodies.

33 Claims, No Drawings

(56) References Cited

FOREIGN PATENT DOCUMENTS

| WO | 2006131013 A2 | 12/2006 |
|---|---|---|
| WO | WO2007/042261 A | 4/2007 |
| WO | WO2007/106744 A2 | 9/2007 |
| WO | WO2007/137984 A2 | 12/2007 |
| WO | 2008061013 A2 | 5/2008 |
| WO | 2008115732 A2 | 9/2008 |
| WO | 2008133722 A2 | 11/2008 |
| WO | 2008144757 A1 | 11/2008 |
| WO | 2009020654 A1 | 2/2009 |
| WO | 2009047356 A1 | 4/2009 |
| WO | 2009091912 A2 | 7/2009 |
| WO | 2009149189 A2 | 12/2009 |
| WO | WO2009/155726 A2 | 12/2009 |
| WO | 2010102251 A2 | 9/2010 |
| WO | 2011059755 A2 | 5/2011 |
| WO | 2011127141 A1 | 10/2011 |
| WO | 2012018790 A2 | 2/2012 |

OTHER PUBLICATIONS

Wu et al. Humanization of a murine monoclonal antibody by simultaneous optimization of framework and CDR residues. J Mol Biol. Nov. 19, 1999;294(1)151-62.*

Hong et al. A humanized anti—4-1BB monoclonal antibody suppresses antigen-induced humoral immune response in nonhuman primates. J Immunother. Nov.-Dec. 2000;23(6):613-21.*

Tempest et al. Efficient generation of a reshaped human mAb specific for the alpha toxin of Clostridium perfringens. Protein Eng. Dec. 1994;7(12):1501-7, Abstract only provided.*

International Search Report and Written Opinion in related application PCT/US2012/061690 mailed Mar. 15, 2013, 20 pages.

International Search Report and Written Opinion in related application PCT/US2012/0061666 mailed Mar. 15, 2013, 22 pages.

Lewiecki, Michael: "Sclerostin monoclonal antibody therapy with AMG 785: a potential treatment for osteoporosis", Expert Opinion on Biological Therapy, Informa Healthcare, UK, vol. 11, No. 1, pp. 117-127 (2011).

International Search Report and Written Opinion in related PCT application PCT/US2012/061686, mailed on Mar. 15, 2013, 24 pages.

Nakanishi, et al., Interleukin-18 regulates Both Th1 and Th2 Responses, Ann. Rev. Immunol. 19: 423-74, (2001).

Arndt and Krauss, Bispecific Diabodies for Cancer Therapy, Methods Mol. Biol. 207: 305-21, (2003).

Durocher et al., "High-level and high-throughput recombinant protein production by transient transfection of suspension-growing human 293-EBNA1 cells", Nucleic Acids Res. 30(2), (2002).

Mizushima and Nagata, "pEF-BOS, a powerful mammalian expression vector", Nucleic Acids Res. 18(17), (1990).

Holliger et al., Diabodies: Small bivalent and bispecific antibody fragments, Proc. Natl. Acad. Sci. USA 90:6444-6448; (1993).

Poljak, et al., Production and structure of diabodies, Structure 2:1121-1123, (1994).

Urlaub and Chasin, "Isolation of Chinese hamster cell mutants deficient in dihydrofolate reductase activity," Proc. Natl. Acad. Sci. USA 77:4216-4220, (1980).

Kaufman and Sharp, Amplfication and Expression of Sequences Cotransfected with a Modular Dihydrofolate Reductase Complementary DNA Gene, Mol. Biol. 159:601-621, (1982).

McDonnell, et al., TNF Antagonism, Progress Respir. Res., 31:247-250, (2001).

Harriman G, et al., Summary of clinical trials in rheumatoid arthritis using infliximab, an anti-TNFalpha treatment, Ann. Rheum. Dis., 58 Suppl 1:I61-4, (1999).

Peng, Experimental Use of Murine Lupus Models, Methods Mol. Med., 102:227-72, (2004).

Bossers, et al., Analysis of Gene Expression in Parkinson's Disease: Possible Involvement of Neurotrophic Support and Axon Guidance in Dopaminergic Cell Death, Brain Pathol., 19: 91-107, (2009).

McGee et al., "The Nogo-66 receptor: focusing myelin inhibition of axon regeneration", Trends Neurosci., 26:193, (2003).

International Search Report, PCT/US2011/31381, dated Aug. 25, 2011, 5 pages.

International Preliminary Report on Patentability, PCT/US2011/31381, dated Mar. 28, 2012, 16 pages.

Extended European Search Report, EP11766636, dated Jan. 14, 2014, 8 pages.

Song et al., "Characterization of a novel anti-human TNF-alpha murine monoclonal antibody with high binding affinity and neutralizing activity," Exp. Mol. Med., Feb. 29; 40(1): 35-42 (2008).

Kapadia et al., "Soluble TNF binding proteins modulate the negative inotropic properties of TNF-alpha in vitro," Am. J. Physiol., 268: H517-H525 (1995).

* cited by examiner

US 9,226,983 B2

TNF-α BINDING PROTEINS

CROSS-REFERENCE TO RELATED APPLICATION

This application claims priority to U.S. Provisional Patent Application No. 61/321,633, filed Apr. 7, 2010, which is hereby expressly incorporated herein by reference in its entirety for any purpose.

FIELD OF THE INVENTION

The present invention relates to TNF-α binding proteins and to their uses in the prevention and/or treatment of acute and chronic immunological diseases such as rheumatoid arthritis, osteoarthritis, psoriasis, multiple sclerosis, and other autoimmune diseases.

BACKGROUND OF THE INVENTION

There is a need in the art for improved antibodies capable of binding TNF-α (also referred to as tumor necrosis factor, tumor necrosis factor-alpha, tumor necrosis factor-α, TNF, and cachectin). In an embodiment, the antibodies are capable of neutralizing TNF-α. The present invention provides a novel family of binding proteins, CDR grafted antibodies, humanized antibodies, and fragments thereof, capable of binding TNF-α, binding TNF-α with high affinity, and binding and neutralizing TNF-α.

SUMMARY OF THE INVENTION

This invention pertains to TNF-α binding proteins, particularly anti-TNF-α antibodies, or antigen-binding portions thereof, that bind TNF-α. In an embodiment, the antibody, or antigen binding portion thereof, capable of binding TNF-α comprises an amino acid sequence selected from the group consisting of SEQ ID NOs: 22-36.

In one aspect, the invention provides a humanized binding protein comprising an antigen binding domain capable of binding human TNF-α, the antigen binding domain comprising at least one CDR comprising an amino acid sequence selected from the group consisting of: residues 31-35 of SEQ ID NO:22; residues 50-65 of SEQ ID NO:22; residues 98-106 of SEQ ID NO:22; residues 24-34 of SEQ ID NO:23; residues 50-56 of SEQ ID NO:23; and residues 89-97 of SEQ ID NO:23, wherein the binding protein comprises a human acceptor framework. In an embodiment, the binding protein comprises at least 3 CDRs, for example, comprises a variable domain CDR set selected from the group consisting of: (a) residues 31-35 of SEQ ID NO:22; residues 50-65 of SEQ ID NO:22; and residues 98-106 of SEQ ID NO:22; and (b) residues 24-34 of SEQ ID NO:23; residues 50-56 of SEQ ID NO:23; and residues 89-97 of SEQ ID NO:23. In particular embodiments, the antigen binding domain comprises an amino acid sequence comprising residues 31-35 of SEQ ID NO:22; residues 50-65 of SEQ ID NO:22; residues 98-106 of SEQ ID NO:22; residues 24-34 of SEQ ID NO:23; residues 50-56 of SEQ ID NO:23; and residues 89-97 of SEQ ID NO:23.

In an embodiment, the antigen binding domain comprises a VH region, for example, comprising an amino acid sequence selected from the group consisting of: SEQ ID NOs: 24, 25, 28, 29, 30, 31, 32, and 33. In another embodiment, the antigen binding domain comprises a VL region, for example, comprising an amino acid sequence selected from the group consisting of: SEQ ID NOs: 26, 27, 34, 35, and 36. In a particular embodiment, the antigen binding domain comprises a VH region and a VL region, for example, wherein the VH region comprises an amino acid sequence selected from the group consisting of: SEQ ID NOs: 24, 25, 28, 29, 30, 31, 32, and 33 and the VL region comprises an amino acid sequence selected from the group consisting of: SEQ ID NOs: 26, 27, 34, 35, and 36.

In an embodiment, the human acceptor framework comprises at least one amino acid sequence selected from the group consisting of: SEQ ID NOs: 6-21. In a particular embodiment, the human acceptor framework comprises an amino acid sequence selected from the group consisting of: SEQ 1N NOs: 9, 10, 11, 12, 15, 16, 17, and 21. In another embodiment, the human acceptor framework comprises at least one framework region amino acid substitution, wherein the amino acid sequence of the framework is at least 65% identical to the sequence of the human acceptor framework and comprises at least 70 amino acid residues identical to the human acceptor framework. In another embodiment, the human acceptor framework comprises at least one framework region amino acid substitution at a key residue, the key residue selected from the group consisting of: a residue adjacent to a CDR; a glycosylation site residue; a rare residue; a residue capable of interacting with human TNF-α; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. In an embodiment, the key residue is selected from the group consisting of: H1, H12, H24, H27, H29, H37, H48, H49, H67, H71, H73, H76, H78, L13, L43, L58, L70, and L80. In an embodiment, the VH mutation is selected from the group consisting of: Q1E, I12V, A24V, G27F, I29L, V29F F29L I37V, I48L, V48L, S49G, V67L, F67L, V71K, R71K, T73N, N76S, L78I, and F78I. In another embodiment, the VL mutation is selected from the group consisting of: V13L, A43S, I58V, E70D, and S80P. In an embodiment, the binding protein comprises two variable domains, wherein the two variable domains have amino acid sequences selected from the group consisting of: SEQ ID NO:24 and SEQ ID NO:26; SEQ ID NO:24 and SEQ ID NO:27; SEQ ID NO:25 and SEQ ID NO:26; SEQ ID NO:25 and SEQ ID NO:27.

In an embodiment, the binding protein binds TNF-α. In another embodiment, the binding protein modulates a biological function of TNF-α. In another embodiment, the binding protein neutralizes TNF-α. In yet another embodiment, the binding protein diminishes the ability of TNF-α to bind to its receptor, for example, the binding protein diminishes the ability of pro-human TNF-α, mature-human TNF-α, or truncated-human TNF-α to bind to its receptor. In yet another embodiment, the binding protein reduces one or more TNF-α biological activities selected from the group consisting of: TNF-dependent cytokine production; TNF-dependent cell killing; TNF-dependent inflammation; TNF-dependent bone erosion; and TNF-dependent cartilage damage.

In an embodiment, the binding protein has an on rate constant ($K_{on}$) selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$; as measured by surface plasmon resonance. In another embodiment, the binding protein has an off rate constant ($K_{off}$) selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance. In yet another embodiment, the binding protein has a dissociation constant ($K_D$) selected from the group consisting of: at most about $10^{-7}$ M; at most about $10^{-8}$ M; at most about $10^{-9}$ M; at most about $10^{-9}$ M; at most about $10^{-11}$ M; at most about $10^{-12}$ M; and at most $10^{-13}$ M.

In an embodiment, the binding protein comprises a heavy chain immunoglobulin constant domain selected from the group consisting of: a human IgM constant domain, a human IgG1 constant domain, a human IgG2 constant domain, a human IgG3 constant domain, a human IgG4 constant domain, a human IgA constant domain, and a human IgE constant domain. In a particular embodiment, the heavy chain immunoglobulin constant region domain is a human IgG1 constant domain. In another embodiment, the binding protein further comprises a light chain immunoglobulin constant domain selected from the group consisting of: a human Ig kappa constant domain and a human Ig lambda constant domain. For example, in an embodiment, the binding domain comprises an immunoglobulin constant domain having an amino acid sequence selected from the group consisting of: SEQ ID NO:2, SEQ ID NO:3, SEQ ID NO:4, and SEQ ID NO:5. In a particular embodiment, the human IgG1 constant domain comprises an amino acid sequence selected from the group consisting of SEQ ID NO:2 and SEQ ID NO:3. In another embodiment, the light chain immunoglobulin constant region domain is a human Ig kappa constant domain comprising an amino acid sequence of SEQ ID NO:4. In yet another embodiment, the light chain immunoglobulin constant region domain is a human Ig lambda constant domain comprising an amino acid sequence SEQ ID NO:5.

In a particular embodiment, the invention provides a binding protein capable of binding human TNF-α, the binding protein comprising: an Ig constant heavy region having an amino acid sequence selected from the group consisting of SEQ ID NO:2 and SEQ ID NO: 3; an Ig constant light region having an amino acid sequence selected from the group consisting of SEQ ID NO:4 and SEQ ID NO: 5; an Ig variable heavy region having an amino acid sequence selected from the group consisting of: SEQ ID NO: 24, 25, 28, 29, 30, 31, 32, and 33; and an Ig variable light region having an amino acid sequence selected from the group consisting of: SEQ ID NO: 26, 27, 34, 35, and 36. In a particular embodiment, the binding protein of the invention is selected from the group consisting of: an immunoglobulin molecule, an Fv, a disulfide linked Fv, a scFv, a monoclonal antibody, an scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a DVD-Ig™, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), and a single chain antibody.

In another aspect, the invention provides a crystallized binding protein comprising a binding protein of the invention, wherein the binding protein is in the form of a crystal. In an embodiment, the crystal is a carrier-free pharmaceutical controlled release crystal. In another embodiment, the binding protein has a greater half life in vivo than the soluble counterpart of the binding protein. In another embodiment, the binding protein retains biological activity.

In another aspect, the invention provides a composition for the release of a TNF-α binding protein, the composition comprising: (a) a formulation, wherein the formulation comprises a crystallized binding protein of the invention and an ingredient; and (b) at least one polymeric carrier. In an embodiment, the polymeric carrier is a polymer selected from one or more of the group consisting of: poly acrylic acid, poly cyanoacrylate, a poly amino acid, a poly anhydride, a poly depsipeptide, a poly ester, poly lactic acid, poly lactic-co-glycolic acid, poly b-hydroxybutryate, poly caprolactone, poly dioxanone; poly ethylene glycol, poly hydroxypropyl methacrylamide, poly organophosphazene, poly ortho esters, poly vinyl alcohol, poly vinylpyrrolidone, maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, and blends and copolymers thereof. In another embodiment, the ingredient is selected from the group consisting of albumin, sucrose, trehalose, lactitol, gelatin, hydroxypropyl-β-cyclodextrin, methoxy-polyethylene glycol and polyethylene glycol.

In another aspect, the invention provides a TNF-α binding protein construct comprising the TNF-α binding protein of the invention and a polypeptide selected from the group consisting of a linker and an immunoglobulin constant domain. In an embodiment, the binding protein possesses a human glycosylation pattern. In another embodiment, the binding protein construct is a crystallized TNF-α binding protein construct. In yet another embodiment, the crystallized TNF-α binding protein construct is a carrier-free pharmaceutical controlled release crystallized TNF-α binding protein construct. In a particular embodiment, the TNF-α binding protein construct has a greater half life in vivo than the soluble counterpart of the binding protein construct. In another embodiment, the binding protein construct retains biological activity.

In another aspect, the invention provides a TNF-α binding protein conjugate comprising a TNF-α binding protein construct of the invention and further comprising an agent selected from the group consisting of: an immunoadhesion molecule, an imaging agent, a therapeutic agent, and a cytotoxic agent. In an embodiment, the agent is an imaging agent selected from the group consisting of a radiolabel, an enzyme, a fluorescent label, a luminescent label, a bioluminescent label, a magnetic label, and biotin. In an embodiment, the imaging agent is a radiolabel selected from the group consisting of: $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In another embodiment, the agent is a therapeutic or cytotoxic agent selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

In another aspect, the invention provides an isolated nucleic acid encoding a binding protein of the invention. In another aspect, the invention provides a vector comprising an isolated nucleic acid of the invention. In an embodiment, the vector is selected from the group consisting of pcDNA, pTT, pTT3, pEFBOS, pBV, pJV, and pBJ. In an embodiment, the invention provides a host cell comprising a vector of the invention. In another embodiment, the host cell is a prokaryotic cell, e.g., *E. coli*. In another embodiment, the host cell is a eukaryotic cell, e.g., a protist cell, an animal cell, a plant cell, or a fungal cell. In another embodiment, the eukaryotic cell is an animal cell selected from the group consisting of a mammalian cell, an avian cell, and an insect cell. For example, the host cell is a CHO cell, a COS cell, a yeast cell, e.g., *Saccharomyces cerevisiae*, or an insect Sf9 cell.

In another aspect, the invention provides a method of producing a protein that binds TNF-α, the method comprising the steps of culturing a host cell of the invention in culture medium under conditions sufficient to produce a binding protein that binds TNF-α as well as a TNF-α binding protein produced by the method.

In another aspect, the invention provides a pharmaceutical composition comprising a binding protein of the invention and a pharmaceutically acceptable carrier. In an embodiment, the pharmaceutically acceptable carrier functions as an adjuvant useful to increase the absorption or dispersion of the binding protein. In another embodiment, the adjuvant is hyaluronidase. In another embodiment, the pharmaceutical composition further comprises at least one additional therapeutic agent for treating a disorder in which TNF-α activity is detrimental, for example, a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof, methotrexate, cyclosporine, rapamycin, FK506, a detectable label, a detectable reporter, a TNF-α antagonist, an anti-rheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive agent, a growth hormone, a hormone replacement drug, a radiopharmaceutical, an antidepressant, an antipsychotic, a stimulant, an asthma medication, a beta agonist, an inhaled steroid, an oral steroid, an epinephrine or analog thereof, a cytokine, and a cytokine antagonist.

In another aspect, the invention provides a method for treating a mammal comprising the step of administering to the mammal an effective amount of the pharmaceutical composition of the invention. In another embodiment, the invention provides a method for reducing human TNF-α activity, the method comprising the step of: contacting human TNF-α with the binding protein of the invention such that human TNF-α activity is reduced. In another embodiment, the invention provides a method for reducing human TNF-α activity in a human subject suffering from a disorder in which TNF-α activity is detrimental, the method comprising the step of administering to the human subject the binding protein of the invention such that human TNF-αactivity in the human subject is reduced. In another embodiment, the invention provides a method for treating a subject for a disease or a disorder in which TNF-α activity is detrimental, the method comprising the step of administering to the subject the binding protein of the invention such that treatment is achieved.

In another embodiment, the invention provides a method of treating a patient suffering from a disorder in which TNF-α is detrimental comprising the step of administering the binding protein of the invention before, concurrent, or after the administration of a second agent, wherein the second agent is selected from the group consisting of an antibody, or fragment thereof, capable of binding human IL-12; PGE2; LPA; NGF; CGRP; SubP; RAGE; histamine; a histamine receptor blocker; bradykinin; IL-1 alpha; IL-1beta; VEGF; PLGF; methotrexate; a corticosteroid, a glucocorticoid receptor modulator; cyclosporin, rapamycin, FK506, a non-steroidal anti-inflammatory agent, and sclerostin, In an embodiment, the disorder is selected from the group consisting of a respiratory disorder; asthma; allergic and nonallergic asthma; asthma due to infection; asthma due to infection with respiratory syncytial virus (RSV); chronic obstructive pulmonary disease (COPD); a condition involving airway inflammation; eosinophilia; fibrosis and excess mucus production; cystic fibrosis; pulmonary fibrosis; an atopic disorder; atopic dermatitis; urticaria; eczema; allergic rhinitis; allergic enterogastritis; an inflammatory and/or autoimmune condition of the skin; an inflammatory and/or autoimmune condition of gastrointestinal organs; inflammatory bowel diseases (IBD); ulcerative colitis; Crohn's disease; an inflammatory and/or autoimmune condition of the liver; liver cirrhosis; liver fibrosis; liver fibrosis caused by hepatitis B and/or C virus; scleroderma; tumors or cancers; hepatocellular carcinoma; glioblastoma; lymphoma; Hodgkin's lymphoma; a viral infection; a bacterial infection; a parasitic infection; HTLV-1 infection; suppression of expression of protective type 1 immune responses, and suppression of expression of a protective type 1 immune response during vaccination. In an embodiment, the disorder is selected from the group consisting of: rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleostasis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma) Abetalipoproteinemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, corpulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic arteriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis (A), His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant Lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Menzel, Dejerine-Thomas, Shy-Drager, and Machado-Joseph), myasthenia gravis, mycobacterium avium intracellulare, mycobacterium tuberculosis, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkins lymphoma, occlusion of the abdominal aorta and its branches, occlusive arterial disorders, OKT3® therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, Subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia greata, anaphylaxis, anti-phospholipid antibody syndrome, aplastic anemia, arteriosclerosis, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, conjunctivitis, childhood onset psychiatric disorder, chronic obstructive pulmonary disease (COPD), dacryocystitis, dermatomyositis, diabetic retinopathy, diabetes mellitus, disk herniation, disk prolapse, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier disease, Landry's paralysis, Langerhan's cell histiocytosis, livedo reticularis, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, ovarian cancer, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, sapho (synovitis, acne, pustulosis, hyperostosis, and osteitis), scleroderma, secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor necrosis factor receptor associated periodic syndrome), type I allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, wound healing, yersinia and salmonella associated arthropathy.

In another embodiment, the invention provides a method of treating a patient suffering from a disorder in which TNF-α is detrimental, the method comprising the step of administering the binding protein of the invention before, concurrent, or after the administration of a second agent, wherein the second agent is selected from the group consisting of inhaled steroids; beta-agonists; short-acting or long-acting beta-agonists; antagonists of leukotrienes or leukotriene receptors; ADVAIR; IgE inhibitors; anti-IgE antibodies; XOLAIR; phosphodiesterase inhibitors; PDE4 inhibitors; xanthines; anticholinergic drugs; mast cell-stabilizing agents; Cromolyn; IL-4 inhibitors; IL-5 inhibitors; eotaxin/CCR3 inhibitors; antagonists of histamine or its receptors including H1, H2, H3, and H4; antagonists of prostaglandin D or its receptors DP1 and CRTH2; TNF antagonists; a soluble fragment of a TNF receptor; ENBREL; TNF enzyme antagonists; TNF converting enzyme (TACE) inhibitors; muscarinic receptor antagonists; TGF-beta antagonists; interferon gamma; perfenidone; chemotherapeutic agents, methotrexate; leflunomide; sirolimus (rapamycin) or an analog thereof, CCI-779; COX2 or cPLA2 inhibitors; NSAIDs; immunomodulators; p38 inhibitors; TPL-2, MK-2 and NFkB inhibitors; budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β antibodies; anti-IL-6 antibodies; growth factors; elastase inhibitors; pyridinyl-imidazole compounds; antibodies or agonists of LT, IL-1, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibodies of CD2, CD3, CD4, CD8, CD25, CD28, CD30, CD40, CD45, CD69, CD90 or their ligands; FK506; rapamycin; mycophenolate mofetil; ibuprofen; prednisolone; phosphodiesterase inhibitors; adensosine agonists; antithrombotic agents; complement inhibitors; adrenergic agents; IRAK, NIK, IKK, p38, or MAP kinase inhibitors; IL-1β converting enzyme inhibitors; TNF-α converting enzyme inhibitors; T-cell signaling inhibitors; metalloproteinase inhibitors; 6-mercaptopurines; angiotensin converting enzyme inhibitors; soluble cytokine receptors; soluble p55 TNF receptor; soluble p75 TNF receptor; sIL-1RI; sIL-1RII; sIL-6R; anti-inflammatory cytokines; IL-4; IL-10; IL-11; and TGF-β.

In an embodiment, the binding protein of the invention is administered to the subject by at least one mode selected from the group consisting of parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

DETAILED DESCRIPTION OF THE INVENTION

This invention pertains to TNF-α binding proteins, particularly anti-TNF-α antibodies, or antigen-binding portions thereof, that bind TNF-α (i.e., tumor necrosis factor, tumor necrosis factor-alpha, tumor necrosis factor-α, TNF, cachectin). Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human TNF-α, to inhibit human TNF-α either in vitro or in vivo, and to regulate gene expression or TNF-α related functions are also encompassed by the invention. Compositions comprising the antibodies of the present invention, as well as methods of using such antibodies, are also described.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or", unless stated otherwise. Furthermore, the use of the term "including", as well as other forms of the term, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, pathology, oncology, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" refers to the process of rendering a chemical species such as a polypeptide substantially free of naturally associated components by isolation, e.g., using protein purification techniques well known in the art.

The term "human TNF-α" (abbreviated herein as hTNF-α), includes a trimeric cytokine protein. The term includes a homotrimeric protein comprising three 17.5 kD TNF-α proteins. The homotrimeric protein is referred to as a "TNF-α protein". The term human "TNF-α" is intended to include recombinant human TNF-α (rhTNF-α) which can be prepared by standard recombinant expression methods. The sequence of human TNF-α is shown in Table 1.

TABLE 1

Sequence of Human TNFα

| Protein | Sequence Identifier | Sequence<br>123456789012345678901234567890123456789012 |
|---|---|---|
| Human TNF-α | SEQ ID NO.: 1 | VRSSSRTPSDKPVAHVVANPQAEGQLQWLNDR |
| | | ANALLANGVELRDNQLVVPSEGLYLIYSQVLF |
| | | KGQGCPSTHVLLTHTISRIAVSYQTKVNLLSA |
| | | IKSPCQRETPEGAEAKPWYEPIYLGGVFQLEK |
| | | GDRLSAEINRPDYLDFAESGQVYFGIIAL |

"Biological activity" refers to all inherent biological properties of the cytokine. Biological properties of TNF-α include but are not limited to binding TNF receptor.

The terms "specific binding" or "specifically binding", in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" or "antigen-binding region" of an antibody (or simply "antibody portion"), refers to one or more fragments of an antibody that retain the ability to specifically bind to an antigen (e.g., hTNF-α). The antigen-binding function of an antibody can be performed by fragments of a full-length antibody. Such antibody embodiments may also have bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546, Winter et al., PCT publication WO 90/05144 A1), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, et al. (1993) Proc. Natl. Acad. Sci. USA 90:6444-6448; Poljak, et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" refers to a polypeptide comprising one or more antigen-binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, et al. (1993) Proc. Natl. Acad. Sci. USA 90:6444-6448; Poljak, et al. (1994) Structure 2:1121-1123). An immunoglobulin constant domain refers to a heavy or light chain constant domain. Human IgG heavy chain and light chain constant domain amino acid sequences are known in the art and represented in Table 2.

TABLE 2

Sequence of Human IgG Heavy Chain Constant Domain and Light Chain Constant Domain

| Protein | Sequence Identifier | Sequence 123456789012345678901234567890012 |
|---|---|---|
| Ig gamma-1 constant region | SEQ ID NO.: 2 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO.: 3 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO.: 4 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |

TABLE 2-continued

Sequence of Human IgG Heavy Chain Constant Domain and Light Chain Constant Domain

| Protein | Sequence Identifier | Sequence<br>123456789012345678901234567890123 |
|---|---|---|
| Ig Lambda constant region | SEQ ID NO.: 5 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

An antibody, or antigen-binding portion thereof, may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, et al. (1995) *Hum. Antibod. Hybridomas* 6:93-101) and use of a cysteine residue, a marker peptide and a C-terminal polyhistidine tag to make bivalent and biotinylated scFv molecules (Kipriyanov, et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody" refers to an antibody, or antigen-binding portion thereof, that is substantially free of other antibodies having different antigenic specificities (e.g., an isolated antibody that specifically binds hTNF-α is substantially free of antibodies that specifically bind antigens other than hTNF-α). An isolated antibody that specifically binds hTNF-α may, however, have cross-reactivity to other antigens, such as TNF-α molecules from other species. Moreover, an isolated antibody may be substantially free of other cellular material and/or chemicals.

The term "human antibody" includes antibodies, or antigen-binding portion thereof, that having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", is not intended to include antibodies in which CDR sequences derived from the germline of another mammalian species, such as a mouse, have been grafted onto human framework sequences.

The term "recombinant human antibody" is intended to include all human antibodies, or antigen-binding portions thereof, that are prepared, expressed, created or isolated by recombinant means, such as antibodies expressed using a recombinant expression vector transfected into a host cell, antibodies isolated from a recombinant, combinatorial human antibody library (Hoogenboom (1997) *Trends Biotechnol.* 15:62-70; Azzazy and Highsmith (2002) *Clin. Biochem.* 35:425-445; Gavilondo and Larrick (2000) *BioTechniques* 29:128-145; Hoogenboom and Chames (2000) *Immunol. Today* 21:371-378), antibodies isolated from an animal (e.g., a mouse) that is transgenic for human immunoglobulin genes (see, e.g., Taylor et al. (1992) *Nucl. Acids Res.* 20:6287-6295; Kellermann and Green (2002) *Current Opin. Biotechnol.* 13:593-597; Little et al. (2000) *Immunol. Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies, or antigen-binding portions thereof, which comprise heavy and light chain variable region sequences from one species and constant region sequences from another species, such as antibodies having murine heavy and light chain variable regions linked to human constant regions.

The term "CDR-grafted antibody" refers to antibodies, or antigen-binding portions thereof, which comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs (e.g., CDR3) has been replaced with murine CDR sequences.

The term "humanized antibody" refers to antibodies, or antigen-binding portions thereof, which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL frameworks.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad. Sci.* 190:382-391 and Kabat, et al. (1991) *Sequences of Proteins of Immunological Interest*, Fifth Edition, U.S. Department of Health and Human Services, NIH Publication No. 91-3242). See also, Martin, "Protein Sequence and Structure Analysis of Antibody Variable Domains," In Kontermann and Dübel, eds., *Antibody Engineering* (Springer-Verlag, Berlin, 2001), Chapter 31, especially pages 432-433. For the heavy chain variable region, the hypervariable region ranges from amino acid positions 31 to 35 for CDR1, amino acid positions 50 to 65 for CDR2, and amino acid positions 95 to 106 for CDR3. For the light chain variable region, the hypervariable region ranges from amino acid positions 24 to 34 for CDR1, amino acid positions 50 to 56 for CDR2, and amino acid positions 89 to 97 for CDR3.

The terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

The term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) *J. Mol. Biol.* 196:901-917) and Chothia et al. (1989) *Nature* 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (1995) *FASEB J* 9:133-139 and MacCallum (1996) *J. Mol. Biol.* 262(5):732-745. Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although particular embodiments use Kabat or Chothia defined CDRs.

The term "canonical" residue refers to a residue in a CDR or framework that defines a particular canonical CDR structure as defined by Chothia et al. (1987) *J. Mol. Biol.* 196:901-917; Chothia et al. (1992) *J. Mol. Biol.* 227:799-817. According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

The terms "donor" and "donor antibody" refer to an antibody providing one or more CDRs. In a particular embodiment, the donor antibody is an antibody from a species different from the antibody from which the framework regions are obtained or derived. In the context of a humanized antibody, the term "donor antibody" refers to a non-human antibody providing one or more CDRs.

The term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. A FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences listed from V-base (vbase.mrc-cpe.cam.ac.uk/) or from IMGT®, the international ImMunoGeneTics information system® (imgt.cines.fr/textes/IMGTrepertoire/LocusGenes/). In another embodiment of the invention the human heavy chain and light chain acceptor sequences are selected from the sequences described in Table 3 and Table 4.

TABLE 3

Heavy Chain Acceptor Sequences

| SEQ ID No. | Protein region | Sequence 1234567890123456789012345678901 |
|---|---|---|
| SEQ ID NO: 6 | VH4-59 FR1 | QVQLQESGPGLVKPSETLSLTCTVSGGSISS |
| SEQ ID NO: 7 | VH4-59 FR2 | WIRQPPGKGLEWIG |
| SEQ ID NO: 8 | VH4-59 FR3 | RVTISVDTSKNQFSLKLSSVTAADTAVYYCAR |
| SEQ ID NO: 9 | VH3-53 FR1 | EVQLVESGGGLIQPGGSLRLSCAASGFTVSS |

TABLE 3-continued

Heavy Chain Acceptor Sequences

| SEQ ID No. | Protein region | Sequence<br>123456789012345678901234567890123456789012 |
|---|---|---|
| SEQ ID NO: 10 | VH3-53 FR2 | WVRQAPGKGLEWVS |
| SEQ ID NO: 11 | VH3-53 FR3 | RFTISRDNSKNTLYLQMNSLRAEDTAVYYCAR |
| SEQ ID NO: 12 | JH1/JH4/JH5 FR4 | WGQGTLVTVSS |
| SEQ ID NO: 13 | JH2 FR4 | WGRGTLVTVSS |
| SEQ ID NO: 14 | JH6 FR4 | WGQGTTVTVSS |

TABLE 4

Light Chain Acceptor Sequences

| SEQ ID No. | Protein region | Sequence<br>123456789012345678901234567890123456789012 |
|---|---|---|
| SEQ ID NO: 15 | 1-39/O12 FR1 | DIQMTQSPSSLSASVGDRVTITC |
| SEQ ID NO: 16 | 1-39/O12 FR2 | WYQQKPGKAPKLLIY |
| SEQ ID NO: 17 | 1-39/O12 FR3 | GVPSRFSGSGSGTDFTLTISSLQPEDFATYYC |
| SEQ ID NO: 18 | 3-15/L2 FR1 | EIVMTQSPATLSVSPGERATLSC |
| SEQ ID NO: 19 | 3-15/L2 FR2 | WYQQKPGQAPRLLIY |
| SEQ ID NO: 20 | 3-15/L2 FR3 | GIPARFSGSGSGTEFTLTISSLQSEDFAVYYC |
| SEQ ID NO: 21 | JK2 FR4 | FGQGTKLEIKR |

The term "germ line antibody gene" or "gene fragment" refers to an immunoglobulin sequence encoded by non-lymphoid cells that have not undergone the maturation process that leads to genetic rearrangement and mutation for expression of a particular immunoglobulin (see, e.g., Shapiro et al. (2002) Crit. Rev. Immunol. 22(3):183-200; Marchalonis et al. (2001) Adv. Exp. Med. Biol. 484:13-30). One of the advantages provided by various embodiments of the present invention stems from the recognition that germ line antibody genes are more likely than mature antibody genes to conserve essential amino acid sequence structures characteristic of individuals in the species, hence less likely to be recognized as from a foreign source when used therapeutically in that species.

The term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (e.g., N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. The term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In a particular embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including, e.g., IgM, IgG, IgD, IgA and IgE, and any isotype, including without limitation, e.g., IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a particular embodiment, such mutations are not extensive. Usually, at least 80%, at least 85%, at least 90%, and at least 95% of the humanized antibody residues will correspond to those of the parental FR and CDR sequences. The term "consensus framework" refers to the framework region in the consensus immunoglobulin sequence. The term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

The term "Vernier" zone refers to a subset of framework residues that may adjust CDR structure and fine-tune the fit to antigen as described by Foote and Winter (1992) *J. Mol. Biol.* 224:487-499. Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein may be engineered to have the three or more antigen binding sites, and is generally not a naturally occurring antibody. The term "multispecific binding protein" refers to a binding protein capable of binding two or more related or unrelated targets. Dual variable domain (DVD) binding proteins or immunoglobulins (DVD-Ig) as used herein, are binding proteins that comprise two or more antigen binding sites and are tetravalent or multivalent binding proteins. Such DVD-Igs may be monospecific, i.e., capable of binding one antigen or multispecific, i.e., capable of binding two or more antigens. DVD-Ig binding proteins comprising two heavy chain DVD-Ig polypeptides and two light chain DVD-Ig polypeptides are referred to a DVD-Ig. Each half of a DVD-Ig comprises a heavy chain DVD-Ig polypeptide, and a light chain DVD-Ig polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. Pat. No. 7,612,181.

One aspect of the invention pertains to a DVD binding protein comprising binding proteins capable of binding TNF-α. In a particular embodiment, the DVD binding protein is capable of binding TNF-α and a second target.

The term "neutralizing" refers to neutralization of a biological activity of a cytokine when a binding protein specifically binds the cytokine. In a particular embodiment, a neutralizing binding protein is a neutralizing antibody whose binding to hTNF-α results in inhibition of a biological activity of hTNF-α, e.g., the neutralizing binding protein binds hTNF-α and reduces a biologically activity of hTNF-α by at least about 20%, 40%, 60%, 80%, 85% or more. Inhibition of a biological activity of hTNF-α by a neutralizing binding protein can be assessed by measuring one or more indicators of hTNF-α biological activity well known in the art. For example neutralization of the cytoxicity of TNF-α on L929 cells.

In another embodiment, the term "agonizing" refers to an increase of a biological activity of TNF-α when a binding protein specifically binds TNF-α, e.g., hTNF-α. In a particular embodiment, an agonizing binding protein is an agonistic antibody whose binding to TNF-α results in the increase of a biological activity of TNF-α. In a particular embodiment, the agonistic binding protein binds TNF-α and increases a biologically activity of TNF-α by at least about 20%, 40%, 60%, 80%, 85%, 90%, 95, 96%, 97%, 98%, 99%, and 100%. An inhibition of a biological activity of TNF-α by an agonistic binding protein can be assessed by measuring one or more indicators of TNF-α biological activity well known in the art.

The term "activity" includes activities such as the binding specificity/affinity of an antibody for an antigen, for example, an anti-hTNF-α antibody that binds to a TNF-α antigen and/or the neutralizing potency (or agonizing potency) of an antibody, for example, an anti-hTNF-α antibody whose binding to hTNF-α inhibits the biological activity of hTNF-α, e.g., neutralization of the cytoxicity of TNF-α on L929 cells.

The terms "epitope" or "antigenic determinant" refers to a site on an antigen to which an immunoglobulin, e.g., an antibody, or T-cell receptor binds. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from TNF-α are tested for reactivity with the given anti-TNF-α antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also, encompassed by the present invention are antibodies that bind to an epitope on TNF-α which comprises all or a portion of an epitope recognized by the particular antibodies described herein (e.g., the same or an overlapping region or a region between or spanning the region).

Also encompassed by the present invention are antibodies that bind the same epitope and/or antibodies that compete for binding to TNF-α, e.g., human TNF-α, with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as hTNF-α. Numerous types of competitive binding assays are known, for example: solid phase direct or indirect radioimmunoassay (RIA), solid phase direct or indirect enzyme immunoassay (EIA), sandwich competition assay (see Stahli et al. (1983) *Methods in Enzymol.* 9:242); solid phase direct biotin-avidin EIA (see Kirkland et al. (1986) *J. Immunol.* 137:3614); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al. (1988) *Mol. Immunol.* 25(1):7); solid phase direct biotin-avidin EIA (Cheung et al. (1990) *Virol.* 176:546); and direct labeled RIA. (Moldenhauer et al. (1990) *Scand. J. Immunol.* 32:77). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

The term "surface plasmon resonance" refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, et al. (1993) *Ann. Biol. Clin.* 51:19-26; Jönsson, et al. (1991) *Biotechniques* 11:620-627; Jöhnsson, et al. (1995) *J. Mol. Recognit.* 8:125-131; and Jöhnsson, et al. (1991) *Anal. Biochem.* 198:268-277.

The term "$K_{on}$" refers to the on rate constant for association of a binding protein (e.g., an antibody) to the antigen to form, e.g., the antibody/antigen complex as is known in the art. The "Kon" also is known by the terms "association rate constant", or "ka", as used interchangeably herein. This value indicating the binding rate of an antibody to its target antigen or the rate of complex formation between an antibody and antigen also is shown by the equation below:

$$\text{Antibody}(\text{"Ab"}) + \text{Antigen}(\text{"Ag"}) \rightarrow \text{Ab-Ag}$$

The term "$K_{off}$" refers to the off rate constant for dissociation, or "dissociation rate constant", of a binding protein (e.g., an antibody), from the, e.g., antibody/antigen complex as is known in the art. This value indicates the dissociation rate of an antibody from its target antigen or separation of Ab-Ag complex over time into free antibody and antigen as shown by the equation below:

$$\text{Ab} + \text{Ag} \leftarrow \text{Ab-Ag}$$

The term "$K_D$" refers to the "equilibrium dissociation constant" and refers to the value obtained in a titration measurement at equilibrium, or by dividing the dissociation rate constant (koff) by the association rate constant (kon). The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "labeled binding protein" refers to a protein with a label incorporated that provides for the identification of the binding protein. In a particular embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" denotes a chemical compound, a mixture of chemical compounds, a biological macromolecule, or an extract made from biological materials. In a particular embodiment, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal" and "crystallized" refers to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giegé et al., Chapter 1, In *Crystallization of Nucleic Acids and Proteins, A Practical Approach,* 2nd ed., (Ducruix and Giegé, eds.) (Oxford University Press, New York, 1999), pp. 1-16.

The term "polynucleotide" means a polymeric form of two or more nucleotides, either ribonucleotides (RNAs) or deoxyribonucleotides (DNAs) or a modified form of either type of nucleotide. The term includes single and double stranded forms of DNA but in a particular embodiment is double-stranded DNA.

The term "isolated polynucleotide" means a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation" refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell") refers to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell". In a particular embodiment, host cells include prokaryotic and eukaryotic cells selected from any of the Kingdoms of life. Eukaryotic cells include protist, fungal, plant and animal cells. In a particular embodiment, host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al. *Molecular Cloning: A Laboratory Manual* (2d ed., Cold Spring Harbor Laboratory Press, Cold Spring Harbor, N.Y. (1989)).

"Transgenic organism" refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, refers to a change or an alteration in the activity of a molecule of interest (e.g., the biological activity of hTNF-α). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator" is a compound capable of changing or altering an activity or function of a molecule of interest (e.g., the biological activity of hTNF-α). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in international PCT Publication WO 01/83525.

The term "agonist" refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, TNF-α polypeptides or polypeptides, nucleic acids, carbohydrates, or any other molecules that bind to hTNF-α.

The term "antagonist" or "inhibitor" refers to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of TNF-α, e.g., hTNF-α. Antagonists and inhibitors of hTNF-α may include, but are not limited to, proteins, nucleic acids, carbohydrates, or any other molecules, which bind to hTNF-α.

The term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample" is used in its broadest sense herein. A "biological sample", includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Antibodies that Bind Human TNF-α

One aspect of the present invention provides isolated murine monoclonal antibodies, or antigen-binding portions thereof, that bind to TNF-α with high affinity, a slow off rate and high neutralizing capacity. A second aspect of the invention provides chimeric antibodies that bind TNF-α. A third aspect of the invention provides CDR grafted antibodies, or antigen-binding portions thereof, that bind TNF-α. A fourth aspect of the invention provides humanized antibodies, or antigen-binding portions thereof, that bind TNF-α. In a particular embodiment, the antibodies, or portions thereof, are isolated antibodies. In an embodiment, the antibodies of the invention are neutralizing human anti-TNF-α or modulating TNF-α functions.

A. Method of Making Anti-TNF-α Antibodies

Antibodies of the present invention may be made by any of a number of techniques known in the art.

1. Anti-TNF-α Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., eds., "Monoclonal Antibodies and T-Cell Hybridomas," In *Research Monographs in Immunology*, vol. 3 (J. L. Turk, General Editor) (Elsevier, N.Y., 1981), pp. 563-587. The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with a TNF-α antigen. In a particular embodiment, the TNF-α antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. In a particular embodiment, if a polypeptide is being administered, the immunization schedule will involve two or more administrations of the polypeptide, spread out over several weeks.

After immunization of an animal with a TNF-α antigen, antibodies and/or antibody-producing cells may be obtained from the animal. An anti-TNF-α antibody-containing serum is obtained from the animal by bleeding or sacrificing the animal. The serum may be used as it is obtained from the animal, an immunoglobulin fraction may be obtained from the serum, or the anti-TNF-α antibodies may be purified from the serum. Serum or immunoglobulins obtained in this manner are polyclonal, thus having a heterogeneous array of properties.

Once an immune response is detected, e.g., antibodies specific for the antigen TNF-α are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding TNF-α. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a particular embodiment, the myeloma cells do not secrete immunoglobulin polypeptides (a non-secretory cell line). After fusion and antibiotic selection, the hybridomas are screened using TNF-α, or a portion thereof, or a cell expressing TNF-α. In a particular embodiment, the initial screening is performed using an enzyme-linked immunoassay (ELISA) or a radioimmunoassay (RIA), or an ELISA. An example of ELISA screening is provided in international PCT Publication WO 00/37504.

Anti-TNF-α antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a particular embodiment, the hybridomas are mouse hybridomas, as described above. In another particular embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-TNF-α antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-TNF-α Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication WO 92/02551 and Babcook, et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the antigen TNF-α, a subunit of TNF-α, or a fragment thereof, is coupled to sheep red blood cells using a linker, such as biotin, and used to identify single cells that secrete antibodies with specificity for TNF-α. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to TNF-α. The amplified immunoglobulin sequences further can be manipulated in vitro, such as by in vitro affinity maturation methods such as those described in PCT Publication WO 97/29131 and PCT Publication WO 00/56772.

3. Anti-TNF-α Monoclonal Antibodies Using Transgenic Animals

In another embodiment of the instant invention, antibodies are produced by immunizing a non-human animal comprising some, or all, of the human immunoglobulin locus with a TNF-α antigen. In a particular embodiment, the non-human animal is a XENOMOUSE transgenic mouse, an engineered mouse strain that comprises large fragments of the human immunoglobulin loci and is deficient in mouse antibody production. See, e.g., Green et al. (1994) *Nature Genet.* 7:13-21 and U.S. Pat. Nos. 5,916,771; 5,939,598; 5,985,615; 5,998,209; 6,075,181; 6,091,001; 6,114,598 and 6,130,364. See also PCT Publications WO 91/10741, published Jul. 25, 1991; WO 94/02602, published Feb. 3, 1994; WO 96/34096 and WO 96/33735, both published Oct. 31, 1996; WO 98/16654, published Apr. 23, 1998; WO 98/24893, published Jun. 11, 1998; WO 98/50433, published Nov. 12, 1998; WO 99/45031, published Sep. 10, 1999; WO 99/53049, published Oct. 21, 1999; WO 00/09560, published Feb. 24, 2000; and WO 00/37504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See, Mendez et al. (1997) *Nature Genet.* 15:146-156; Green and Jakobovits (1998) *J. Exp. Med.* 188:483-495.

4. Anti-TNF-α Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, U.S. Pat. No. 5,223,409; PCT Publications WO 92/18619; WO 91/17271; WO 92/20791; WO 92/15679; WO 93/01288; WO 92/01047; WO 92/09690; and WO 97/29131; Fuchs et al. (1991) *Bio/Technology* 9:1369-1372; Hay et al. (1992) *Hum. Antibod. Hybridomas* 3:81-85; Huse et al. (1989) *Science* 246:1275-1281; McCafferty et al. (1990) *Nature* 348:552-554; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) Bio/Technology 9:1373-1377; Hoogenboom et al. (1991) *Nucl. Acid Res.* 19:4133-4137; and Barbas et al. (1991) *Proc. Natl. Acad. Sci. USA* 88:7978-7982; and U.S. Patent Publication No. 2003.0186374.

The recombinant antibody library may be from a subject immunized with TNF-α, or a portion of TNF-α. Alternatively, the recombinant antibody library may be from a naïve subject, i.e., one who has not been immunized with TNF-α, such as a human antibody library from a human subject who has not been immunized with human TNF-α. Antibodies of the invention are selected by screening the recombinant antibody library with the peptide comprising human TNF-α to thereby select those antibodies that recognize TNF-α. Methods for conducting such screening and selection are well known in the art, such as described in the references in the preceding paragraph. To select antibodies of the invention having particular binding affinities for hTNF-α, such as those that dissociate from human TNF-α with a particular $k_{off}$ rate constant, the art-known method of surface plasmon resonance can be used to select antibodies having the desired $k_{off}$ rate constant. To select antibodies of the invention having a particular neutralizing activity for hTNF-α, such as those with a particular an $IC_{50}$, standard methods known in the art for assessing the inhibition of hTNF-α activity may be used.

In one aspect, the invention pertains to an isolated antibody, or an antigen-binding portion thereof, that binds TNF-α, e.g., human TNF-α. In a particular embodiment, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkmann et al. (1995) *J. Immunol. Methods* 182:41-50; Ames et al. (1995) *J. Immunol. Methods* 184:177-186; Kettleborough et al. (1994) *Eur. J. Immunol.* 24:952-958; Persic et al. (1997) *Gene* 187 9-18; Burton et al. (1994) *Adv. Immunol.* 57:191-280; PCT Publications WO 90/02809; WO 91/10737; WO 92/01047 (PCT Application No. PCT/GB91/01134); WO 92/18619; WO 93/11236; WO 95/15982; and WO 95/20401; and U.S. Pat. Nos. 5,698,426; 5,223,409; 5,403,484; 5,580,717; 5,427,908; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT Publication WO 92/22324; Mullinax et al. (1992) *BioTechniques* 12(6):864-869; and Sawai et al. (1995) *Am. J. Reprod. Immunol.* 34:26-34; and Better et al. (1998) *Science* 240:1041-1043. Examples of techniques which can be used to produce single-chain Fvs and antibodies include those described in U.S. Pat. Nos. 4,946,778 and 5,258,498; Huston et al. (1991) *Methods Enzymol.* 203:46-88; Shu et al. (1993) *Proc. Natl. Acad. Sci. USA* 90:7995-7999; and Skerra et al. (1998) *Science* 240:1038-1041.

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 and in Roberts and Szostak (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup et al. U.S. Pat. No. 6,699,658 and Frenken et al., U.S. Pat. No. 6,114,147.

B. Production of Recombinant TNF-α Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is contemplated, for example, in mammalian host cells, because such eukaryotic cells (and in particular mammalian cells) are more likely than prokaryotic cells to assemble and secrete a properly folded and immunologically active antibody.

Mammalian host cells for expressing the recombinant antibodies of the invention include Chinese Hamster Ovary (CHO cells) (including dhfr- CHO cells, described in Urlaub and Chasin (1980) *Proc. Natl. Acad. Sci. USA* 77:4216-4220, used with a DHFR selectable marker, e.g., as described in Kaufman and Sharp (1982) *J. Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, in particular, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest.

The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In an exemplary system for recombinant expression of an antibody, or antigen-binding portion thereof, of the invention, a recombinant expression vector encoding both the antibody heavy chain and the antibody light chain is introduced into dhfr− CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti hTNF-α Antibodies

Table 5 is a list of amino acid sequences of VH and VL regions (CDR sequences bolded) of anti-hTNF-α antibodies of the invention.

TABLE 5

List of Amino Acid Sequences of Murine
Anti-hTNF-α Antibody VH And VL Regions

| SEQ ID NO. | Protein region | | Sequence 12345678901234567890123456789 0 |
|---|---|---|---|
| 22 | VH MAK195 | | QVQLKESGPGLVAPSQSLSITCTVSGFSLT DYGVNWVRQPPGKGLEWLGMIWGDGSTDYD STLKSRLSISKDNSKSQIFLKMNSLQTDDT ARYYCAREWHHGPVAYWGQGTLVTVSA |
| | VH MAK195CDR-H1 | Residues 31-35 of SEQ ID NO: 22 | DYGVN |
| | VH MAK195CDR-H2 | Residues 50-65 of SEQ ID NO: 22 | MIWGDGSTDYDSTLKS |
| | VH MAK195CDR-H3 | Residues 98-106 of SEQ ID NO: 22 | EWHHGPVAY |
| 23 | VL MAK195 | | DIVMTQSHKFMSTTVGDRVSITCKASQAVS SAVAWYQQKPGQSPKLLIYWASTRHTGVPD RFTGSGSVTDFTLTIHNLQAEDLALYYCQQ HYSTPFTFGSGTKLEIKR |
| | VL MAK195CDR-L1 | Residues 24-34 of SEQ ID NO: 23 | KASQAVSSAVA |
| | VL MAK195CDR-L2 | Residues 50-56 of SEQ ID NO: 23 | WASTRHT |
| | VL MAK195CDR-L3 | Residues 89-97 of SEQ ID NO: 23 | QQHYSTPFT |

2. Anti-hTNF-α Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail in Example 2.1. See, e.g., Morrison (1985) Science 229:1202; Oi et al. (1986) BioTechniques 4:214-221; Gillies et al. (1989) J. Immunol. Methods 125:191-202; U.S. Pat. Nos. 5,807,715; 4,816,567; and 4,816,397. In addition, techniques developed for the production of "chimeric antibodies" (Morrison et al. (1984) Proc. Natl. Acad. Sci. USA 81:6851-6855; Neuberger et al. (1984), Nature 312:604-608; Takeda et al. (1985) Nature 314:452-454; by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti human TNF-α antibodies described in section 1 with a human IgG1 constant region.

3. Anti-TNF-α CDR-Grafted Antibodies

CDR-grafted antibodies of the invention comprise heavy and light chain variable region sequences from a human antibody wherein one or more of the CDR regions of VH and/or VL are replaced with CDR sequences of the murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, in an embodiment, the human variable framework that is chosen to replace the murine variable framework apart from the CDRs have at least a 65% sequence identity with the murine antibody variable region framework. In a particular embodiment, the human and murine variable regions apart from the CDRs have at least 70% sequence identify. In a particular embodiment, the human and murine variable regions apart from the CDRs have at least 75% sequence identity. In a particular embodiment, the human and murine variable regions apart from the CDRs have at least 80% sequence identity. Methods for producing chimeric antibodies are known in the art and discussed in detail in Example 2.2. (also see EP Patent No. EP 0 239 400; PCT Publication WO 91/09967; U.S. Pat. Nos. 5,225,539; 5,530,101; and 5,585,089), veneering or resurfacing (EP 0 592 106; EP 0 519 596; Padlan (1991) *Mol. Immunol.* 28(4/5):489-498; Studnicka et al. (1994) *Protein Eng.* 7(6):805-814; Roguska et al. (1994) *Proc. Natl. Acad. Sci. USA* 91:969-973), and chain shuffling (U.S. Pat. No. 5,565, 352).

In a specific embodiment the invention provides CDR grafted antibodies with VH and/or VL chains as described in Table 6.

TABLE 6

CDR Grafted Antibodies

| SEQ ID No. | Protein region | Sequence 12345678901234567890123456789 |
|---|---|---|
| 24 | hMAK195VH.1z | QVQLQESGPGLVKPSETLSLTCTVSGGSIS DYGVNWIRQPPGKGLEWIGMIWGDGSTDYD STLKSRVTISVDTSKNQFSLKLSSVTAADT AVYYCAREWHHGPVAYWCQGTLVTVSS |
| 25 | hMAK195VH.2z | EVQLVESGGGLIQPGGSLRLSCAASGFTVS DYGVNWVRQAPGKGLEWVSMIWGDGSTDYD STLKSRFTISRDNSKNTLYLQMNSLRAEDT AVYYCAREWHHGPVAYWGQGTLVTVSS |
| 26 | hMAK195Vk.1 | DIQMTQSPSSLSASVGDRVTITCKASQAVS SAVAWYQQKPGKAPKLLIYWASTRHTGVPS RFSGSGSGTDFTLTISSLQPEDFATYYCQQ HYSTPFTFGQGTKLEIK |
| 27 | hMAK195Vk.2z | EIVMTQSPATLSVSPGERATLSCKASQAVS SAVAWYQQKPGQAPRLLIYWASTRHTGIPA RFSGSGSGTEFTLTISSLQSEDFAVYYCQQ HYSTPFTFGQGTKLEIK |

4. Anti-hTNF-α Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uniheidelberg.de/SD/IT/IT.html; www.whfreeman.com/immunology/CH-05/kuby05.htm; www.library.thinkquest.org/12429/Immune/Antibody.html; www.hhmi.org/grants/lectures/1996/vlab/; www.path.cam.ac.ukLabout.mrc7/mikeimages.html; www.antibodyresource.com/; mcb.harvard.edu/BioLinks/Immunology.html.www.immunologylink.com/; pathbox.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl.html; www.recab.uni-hd.de/immuno.bme.nwu.edu/; www.mrc-cpe.cam.ac.uk/imt-doc/public/INTRO.html; www.ibt.unam.mx/virN_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.ukLabout.ubcg07s/; www.nimr.mrc.ac.uk/CC/ccaewg/ccaewg.htm; www.path.cam.ac.ukl.about.mrc7/humanisation/TAHHP.html; www.ibt.unam.mx/vir/structure/stat_aim.html; www.biosci.missouri.edu/smithgp/index.html; www.cryst.bioc.cam.ac.uk/.about.fmolina/Web-pages/Pept/spottech.html; wwwjerini.de/fr roducts.htm; www.patents.ibm.com/ibm.html.Kabat et al., Sequences of Proteins of Immunological Interest, U.S. Dept. Health (1983. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; Riechmann et al. (1988) *Nature* 332:323-327.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al. (1986) *Nature* 321:522-525; Verhoeyen et al. (1988) *Science* 239:1534-1536; Sims et al. (1993) *J. Immunol.* 151: 2296-2308; Chothia and Lesk (1987) *J. Mol. Biol.* 196:901-917; Carter et al. (1992) *Proc. Natl. Acad. Sci. USA* 89:4285-4289; Presta et al. (1993) *J. Immu-* nol. 151:2623-2632; Padlan (1991) *Mol. Immunol.* 28(4/5): 489-498; Studnicka et al. (1994) *Protein Engineering* 7(6): 805-814; Roguska. et al. (1994) *Proc. Natl. Acad. Sci. USA* 91:969-973; PCT Publication Nos. WO 91/09967, WO 99/06834 (International Application No. PCT/US98/16280), WO 97/20032 (Appln. No. PCT/US96/18978), WO 92/11272 (Appln. No. PCT/US91/09630), WO 92/03461 (Appln. No. PCT/US91/05939), WO 94/18219 (Appln. No. PCT/US94/01234), WO 92/01047 (Appln. No. PCT/GB91/01134), WO 93/06213 (Appln. No. PCT/GB92/01755), WO 90/14443, WO 90/14424, and WO 90/14430; European Publication Nos. EP 0 592 106, EP 0 519 596, and EP 0 239 400, U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

C. Production of Antibodies and Antibody-Producing Cell Lines

In an embodiment, anti-TNF-α antibodies of the present invention, exhibit a high capacity to reduce or to neutralize TNF-α activity, e.g., as assessed by any one of several in vitro and in vivo assays known in the art. Alternatively, anti-TNF-α antibodies of the present invention, also exhibit a high capacity to increase or agonize TNF-α activity.

In particular embodiments, the isolated antibody, or antigen-binding portion thereof, binds human TNF-α, wherein the antibody, or antigen-binding portion thereof, dissociates from human TNF-α with a $k_{off}$ rate constant of about $0.1 \, s^{-1}$ or less, as determined by surface plasmon resonance, or which inhibits human TNF-α activity with an $IC_{50}$ of about $1 \times 10^{-6}$ M or less. Alternatively, the antibody, or an antigen-binding portion thereof, may dissociate from human TNF-α with a $k_{off}$ rate constant of about $1 \times 10^{-2} \, s^{-1}$ or less, as determined by surface plasmon resonance, or may inhibit human TNF-α activity with an $IC_{50}$ of about $1 \times 10^{-7}$ M or less. Alternatively, the antibody, or an antigen-binding portion thereof, may dissociate from human TNF-α with a $k_{off}$ rate constant of about $1 \times 10^{-3} \, s^{-1}$ or less, as determined by surface plasmon resonance, or may inhibit human TNF-α activity with an $IC_{50}$ of about $1 \times 10^{-8}$ M or less. Alternatively, the antibody, or an antigen-binding portion thereof, may dissociate from human TNF-α with a $k_{off}$ rate constant of about $1 \times 10^{-4} \, s^{-1}$ or less, as determined by surface plasmon resonance, or may inhibit human TNF-α activity with an $IC_{50}$ of about $1 \times 10^{-9}$ M or less. Alternatively, the antibody, or an antigen-binding portion thereof, may dissociate from human TNF-α with a $k_{off}$ rate constant of about $1 \times 10^{-5} \, s^{-1}$ or less, as determined by surface plasmon resonance, or may inhibit human TNF-α activity with an $IC_{50}$ of about $1 \times 10^{-10}$ M or less. Alternatively, the antibody, or an antigen-binding portion thereof, may dissociate from human TNF-α with a $k_{off}$ rate constant of about $1 \times 10^{-5} \, s^{-1}$ or less, as determined by surface plasmon resonance, or may inhibit human TNF-α activity with an $IC_{50}$ of about $1 \times 10^{-11}$ M or less.

In certain embodiments, the antibody comprises a heavy chain constant region, such as an IgG1, IgG2, IgG3, IgG4, IgA, IgE, IgM or IgD constant region. In an embodiment, the heavy chain constant region is an IgG1 heavy chain constant region or an IgG4 heavy chain constant region. Furthermore, the antibody can comprise a light chain constant region, either a kappa light chain constant region or a lambda light chain constant region. In another embodiment, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (See U.S. Pat. Nos. 5,648,260 and 5,624,821). The Fc portion of an antibody mediates several important effector functions, e.g., cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. In an embodiment, the invention relates to crystals of whole anti-TNF-α antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in PCT Publication WO 02/72636.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. In an embodiment, the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Pat. Nos. 7,449,308 and 7,029,872).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. In an embodiment, the protein having a particularly selected novel glycosylation pattern exhibits improved or altered biological properties.

D. Uses of Anti-TNF-α Antibodies

Given their ability to bind to human TNF-α, e.g., the anti-human TNF-α antibodies, or portions thereof, of the invention can be used to detect TNF-α (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting TNF-α in a biological sample comprising contacting a biological sample with an antibody, or antibody portion, of the invention and detecting either the antibody (or antibody portion) bound to TNF-α or unbound antibody (or antibody portion), to thereby detect TNF-α in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human TNF-α can be assayed in biological fluids by a competition immunoassay utilizing rhTNF-α standards labeled with a detectable substance and an unlabeled anti-human TNF-α antibody. In this assay, the biological sample, the labeled rhTNF-α standards and the anti-human TNF-α antibody are combined and the amount of labeled rhTNF-α standard bound to the unlabeled antibody is determined. The amount of human TNF-α in the biological sample is inversely proportional to the amount of labeled rhTNF-α standard bound to the anti-TNF-α antibody. Similarly, human TNF-α can also be assayed in biological fluids by a competition immunoassay utilizing rhTNF-α standards labeled with a detectable substance and an unlabeled anti-human TNF-α antibody.

In an embodiment, the antibodies and antibody portions of the invention are capable of neutralizing TNF-α activity, e.g., human TNF-α activity, both in vitro and in vivo. In another embodiment, the antibodies and antibody portions of the invention are capable of increasing or agonizing human TNF-α activity, e.g., human TNF-α activity. Accordingly, such antibodies and antibody portions of the invention can be used to inhibit or increase hTNF-α activity, e.g., in a cell culture containing hTNF-α, in human subjects or in other mammalian subjects having TNF-α with which an antibody of the invention cross-reacts. In one embodiment, the invention provides a method for inhibiting or increasing hTNF-α activity comprising contacting hTNF-α with an antibody or antibody portion of the invention such that hTNF-α activity is inhibited or increased. For example, in a cell culture containing, or suspected of containing hTNF-α, an antibody or antibody portion of the invention can be added to the culture medium to inhibit or increase hTNF-α activity in the culture.

In another embodiment, the invention provides a method for reducing or increasing hTNF-α activity in a subject, advantageously from a subject suffering from a disease or disorder in which TNF-α-activity is detrimental or, alternatively, beneficial. The invention provides methods for reducing or increasing TNF-α activity in a subject suffering from such a disease or disorder, which method comprises administering to the subject an antibody or antibody portion of the invention such that TNF-α activity in the subject is reduced or increased. In a particular embodiment, the TNF-α is human TNF-α, and the subject is a human subject. Alternatively, the subject can be a mammal expressing a TNF-α to which an antibody of the invention is capable of binding. Still further the subject can be a mammal into which TNF-α has been introduced (e.g., by administration of TNF-α or by expression of a TNF-α transgene). An antibody of the invention can be administered to a human subject for therapeutic purposes. Moreover, an antibody of the invention can be administered to a non-human mammal expressing a TNF-α with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

The term "a disorder in which TNF-α activity is detrimental" includes diseases and other disorders in which the presence of TNF-α activity in a subject suffering from the disorder has been shown to be or is suspected of being either responsible for the pathophysiology of the disorder or a factor that contributes to a worsening of the disorder. Accordingly, a disorder in which TNF-α activity is detrimental is a disorder in which reduction of TNF-α activity is expected to alleviate the symptoms and/or progression of the disorder. Such disorders may be evidenced, for example, by an increase in the concentration of TNF-α in a biological fluid of a subject suffering from the disorder (e.g., an increase in the concentration of TNF-α in serum, plasma, synovial fluid, etc. of the subject), which can be detected, for example, using an anti-TNF-α antibody as described above. Non-limiting examples of disorders that can be treated with the antibodies of the invention include those disorders discussed in the section below pertaining to pharmaceutical compositions of the antibodies of the invention.

Alternatively, the term "a disorder in which TNF-α activity is beneficial" include diseases and other disorders in which the presence of TNF-α activity in a subject suffering from the disorder has been shown to be or is suspected of being either beneficial for treating the pathophysiology of the disorder or a factor that contributes to a treatment of the disorder. Accordingly, a disorder in which TNF-α activity is beneficial is a disorder in which an increase of TNF-α activity is expected to alleviate the symptoms and/or progression of the disorder. Non-limiting examples of disorders that can be treated with the antibodies of the invention include those disorders discussed in the section below pertaining to pharmaceutical compositions of the antibodies of the invention.

E. Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which TNF-α activity is detrimental. In a particular embodiment, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. The term "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, isotonic agents, for example, sugars, polyalcohols such as mannitol, sorbitol, or sodium chloride in the composition, may be included. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu (1987) *J. Biol. Chem.* 262:4429-4432), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; and 5,290,540; and PCT Publication Nos. WO 92/19244, WO 97/32572, WO 97/44013, WO 98/31346, and WO 99/66903. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton (1987) *CRC Crit. Rev. Biomed. Eng.* 14:201-240;

Buchwald et al. (1980) *Surgery* 88:507-516; Saudek et al. (1989) *N. Engl. J. Med.* 321:574-579). In another embodiment, polymeric materials can be used to achieve controlled or sustained release of the therapies of the invention (see e.g., Goodson, J. M., Chapter 6, In *Medical Applications of Controlled Release, Vol. II, Applications and Evaluation*, (Langer and Wise, eds.) (CRC Press, Inc., Boca Raton, 1984), pp. 115-138; *Controlled Drug Bioavailability, Drug Product Design and Performance*, (Smolen and Ball, eds.) (Wiley, New York, 1984); Langer and Peppas (1983) *J. Macromol. Sci. Rev. Macromol. Chem. Phys.* C23(1):61-126; see also Levy et al. (1985) *Science* 228:190-192; During et al. (1989) *Ann. Neurol.* 25:351-356; Howard et al. (1989) *J. Neurosurg.* 71:105-112); U.S. Pat. Nos. 5,679,377; 5,916,597; 5,912,015; 5,989,463; and 5,128,326; and PCT Publications WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, In *Medical Applications of Controlled Release*, Vol. II, supra, pp. 115-138 (1984).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; PCT publication WO 91/05548; PCT publication WO 96/20698, Ning et al. (1996) *Radiotherapy Oncol.* 39:179-189; Song et al. (1996) *PDA J. Pharm. Sci. Technol.* 50:372-377; Cleek et al. (1997) *Proceed. Int'l. Symp. Control. Rel. Bioact. Mater.* 24:853-854, and Lam et al. (1997) *Proceed. Intl. Symp. Control Rel. Bioact. Matter.* 24:759-760.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see, e.g., Joliot et al. (1991) *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences and Introduction to Pharmaceutical Dosage Forms*, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, optionally in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; and 5,290,540; and PCT Publications WO 92/19244, WO 97/32572, WO 97/44013, WO 98/31346, and WO 99/66903. In a specific embodiment, an antibody of the invention, combination therapy, and/or composition of the invention is administered using Alkermes AIR® pulmonary drug delivery technology (Alkermes, Inc., Cambridge, Mass. US).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. In an embodiment, one or more of the prophylactic or therapeutic agents or pharmaceutical compositions of the invention is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. In an embodiment, the liquid form of the administered composition is supplied in a hermetically sealed container at least 0.25 mg/ml, at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. In an embodiment, the antibody or antibody-portions will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The particular form depends on the intended mode of administration and therapeutic application. Typical compositions are in the form of injectable or infusible solutions, such as compositions similar to those used for passive immunization of humans with other antibodies. The mode of administration includes parenteral (e.g., intravenous, subcutaneous, intraperitoneal, intramuscular). In a particular embodiment, the antibody is administered by intravenous infusion or injection. In another particular embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation include vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, for example, the route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which TNF-α activity is detrimental. For example, an anti-hTNF-α antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to TNF-α or fragment thereof is linked to a half-life extending vehicle known in the art. Such vehicles include, but are not limited to, the Fc domain, polyethylene glycol, and dextran. Such vehicles are described, e.g., in U.S. Pat. No. 6,660,843.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al. (1993) *Clin. Pharm.* 12:488-505; Wu and Wu (1991) *Biotherapy* 3:87-95; Tolstoshev (1993) *Ann. Rev. Pharmacol. Toxicol.* 32:573-596; Mulligan (1993) *Science* 260:926-932; and Morgan and Anderson (1993) *Ann. Rev. Biochem.* 62:191-217; Robinson (1993) *Trends Biotechnol.* 11(5):155. Methods commonly known in the art of recombinant DNA technology which can be used are described in Ausubel et al. (eds.), *Current Protocols in Molecular Biology*, John Wiley &Sons, NY (1993); and Kriegler, *Gene Transfer and Expression, A Laboratory Manual*, Stockton Press, NY (1990). Detailed descriptions of various methods of gene therapy are disclosed in U.S. Patent Publication No. 2009/0297514.

TNF-α plays a critical role in the pathology associated with a variety of diseases involving immune and inflammatory elements. These diseases include, but are not limited to, Acquired Immunodeficiency Disease Syndrome; Acquired Immunodeficiency Related Diseases; acquired pernicious anaemia; acute coronary syndromes; acute and chronic pain (different forms of pain); acute idiopathic polyneuritis; acute immune disease associated with organ transplantation; acute or chronic immune disease associated with organ transplantation; acute inflammatory demyelinating polyradiculoneuropathy; acute ischemia; acute liver disease; acute rheumatic fever; acute transverse myelitis; Addison's disease; adult (acute) respiratory distress syndrome; Adult Still's Disease; alcoholic cirrhosis; alcohol-induced liver injury; allergic diseases; allergy; alopecia; alopecia greata; Alzheimer's disease; anaphylaxis; ankylosing spondylitis; ankylosing spondylitis associated lung disease; Anti-Phospholipid Antibody Syndrome; aplastic anemia; arteriosclerosis; arthropathy; asthma; atheromatous disease/arteriosclerosis; atherosclerosis; atopic allergy; atopic eczema; atopic dermatitis; atrophic autoimmune hypothyroidism; autoimmune bullous disease; autoimmune dermatitis; autoimmune diabetes; autoimmune disorder associated with *Streptococcus* infection; autoimmune enteropathy; autoimmune haemolytic anaemia; autoimmune hepatitis; autoimmune hearing loss; Autoimmune Lymphoproliferative Syndrome (ALPS); autoimmune mediated hypoglycaemia; autoimmune myocarditis; autoimmune neutropenia; autoimmune premature ovarian failure; autoimmune thrombocytopenia (AITP); autoimmune thyroid disease; autoimmune uveitis; bronchiolitis obliterans; Behcet's disease; blepharitis; bronchiectasis; bullous pemphigoid; cachexia; cardiovascular disease;

catastrophic antiphospholipid syndrome; celiac disease; cervical spondylosis; chlamydia; choleostasis; chronic active hepatitis; chronic eosinophilic pneumonia; chronic fatigue syndrome; chronic immune disease associated with organ transplantation; chronic ischemia; chronic liver diseases; chronic mucocutaneous candidiasis; cicatricial pemphigoid; clinically isolated syndrome (CIS) with risk for multiple sclerosis; common varied immunodeficiency (common variable hypogammaglobulinaemia); connective tissue disease associated interstitial lung disease; conjunctivitis; Coombs positive haemolytic anaemia; childhood onset psychiatric disorder; chronic obstructive pulmonary disease (COPD); Crohn's disease; cryptogenic autoimmune hepatitis; cryptogenic fibrosing alveolitis; dacryocystitis; depression; dermatitis scleroderma; dermatomyositis; dermatomyositis/polymyositis associated lung disease; diabetic retinopathy; diabetes mellitus; dilated cardiomyopathy; discoid lupus erythematosus; disk herniation; disk prolapse; disseminated intravascular coagulation; drug-induced hepatitis; drug-induced interstitial lung disease; drug induced immune hemolytic anemia; endocarditis; endometriosis; endophthalmitis; enteropathic synovitis; episcleritis; erythema multiforme; erythema multiforme major; female infertility; fibrosis; fibrotic lung disease; gestational pemphigoid; giant cell arteritis (GCA); glomerulonephritides; goitrous autoimmune hypothyroidism (Hashimoto's disease); Goodpasture's syndrome; gouty arthritis; graft versus host disease (GVHD); Grave's disease; group B streptococci (GBS) infection; Guillain-Barré syndrome (GBS); haemosiderosis associated lung disease; hay fever; heart failure; hemolytic anemia; Henoch-Schoenlein purpurea; hepatitis B; hepatitis C; Hughes Syndrome; Huntington's chorea; hyperthyroidism; hypoparathyroidism; idiopathic leucopaenia; idiopathic thrombocytopaenia; idiopathic Parkinson's Disease; idiopathic interstitial pneumonia; idiosyncratic liver disease; IgE-mediated Allergy; Immune hemolytic anemiae; inclusion body myositis; infectious diseases; Infectious ocular inflammatory disease; inflammatory bowel disease; Inflammatory demyelinating disease; Inflammatory heart disease; Inflammatory kidney disease; insulin dependent diabetes mellitus; interstitial pneumonitis; IPF/UIP; iritis; juvenile chronic arthritis; juvenile pernicious anaemia; juvenile rheumatoid arthritis; Kawasaki's disease; keratitis; keratojunctivitis sicca; Kussmaul disease or Kussmaul-Meier Disease; Landry's paralysis; Langerhan's cell histiocytosis; linear IgA disease; livedo reticularis; Lyme arthritis; lymphocytic infiltrative lung disease; macular degeneration; male infertility idiopathic or NOS; malignancies; microscopic vasculitis of the kidneys; microscopic polyangiitis; mixed connective tissue disease associated lung disease; Morbus Bechterev; motor neuron disorders; mucous membrane pemphigoid; multiple sclerosis (all subtypes: primary progressive, secondary progressive, relapsing remitting, etc.); multiple organ failure; myalgic encephalitis/Royal Free Disease; Myasthenia Gravis; myelodysplastic syndrome; myocardial infarction; myocarditis; nephrotic syndrome; nerve root disorders; neuropathy; non-alcoholic steatohepatitis; non-A non-B hepatitis; optic neuritis; organ transplant rejection; osteoarthritis; osteolysis; ovarian cancer; ovarian failure; pancreatitis; parasitic diseases; Parkinson's disease; pauciarticular JRA; pemphigoid; pemphigus foliaceus; pemphigus vulgaris; peripheral artery occlusive disease (PAOD); peripheral vascular disease (PVD); peripheral artery disease (PAD); phacogenic uveitis; phlebitis; polyarteritis nodosa (or periarteritis nodosa); polychondritis; polymyalgia rheumatica; poliosis; polyarticular JRA; polyendocrine deficiency syndrome; polymyositis; polyglandular deficiency type I and polyglandular deficiency type II; polymyalgia rheumatica (PMR); postinfectious interstitial lung disease; post-inflammatory interstitial lung disease; post-pump syndrome; premature ovarian failure; primary biliary cirrhosis; primary myxoedema; primary Parkinsonism; primary sclerosing cholangitis; primary sclerosing hepatitis; primary vasculitis; prostate and rectal cancer and hematopoietic malignancies (leukemia and lymphoma); prostatitis; psoriasis; psoriasis type 1; psoriasis type 2; psoriatic arthritis; psoriatic arthropathy; pulmonary hypertension secondary to connective tissue disease; pulmonary manifestation of polyarteritis nodosa; pure red cell aplasia; primary adrenal insufficiency; radiation fibrosis; reactive arthritis; Reiter's disease; recurrent neuromyelitis optica; renal disease NOS; restenosis; rheumatoid arthritis; rheumatoid arthritis associated interstitial lung disease; rheumatic heart disease; SAPHO (synovitis, acne, pustulosis, hyperostosis, and osteitis); sarcoidosis; schizophrenia; Schmidt's syndrome; scleroderma; secondary amyloidosis; shock lung; scleritis; sciatica; secondary adrenal insufficiency; sepsis syndrome; septic arthritis; septic shock; seronegative arthropathy; silicone associated connective tissue disease Sjögren's disease associated lung disease; Sjögren's syndrome; Sneddon-Wilkinson dermatosis; sperm autoimmunity; spondyloarthropathy; spondylitis ankylosans; Stevens-Johnson Syndrome (SJS); Still's disease; stroke; sympathetic ophthalmia; systemic inflammatory response syndrome; systemic lupus erythematosus; systemic lupus erythematosus associated lung disease; systemic sclerosis; systemic sclerosis associated interstitial lung disease; Takayasu's disease/arteritis; temporal arteritis; Th2 Type and Th1 Type mediated diseases; thyroiditis; toxic shock syndrome; toxoplasmic retinitis; toxic epidermal necrolysis; transverse myelitis; TRAPS (tumor-necrosis factor receptor type 1 (TNFR)-Associated Periodic Syndrome); type B insulin resistance with acanthosis nigricans; Type 1 allergic reaction; type-1 autoimmune hepatitis (classical autoimmune or lupoid hepatitis); type-2 autoimmune hepatitis (anti-LKM antibody hepatitis)$_e$; Type II diabetes; ulcerative colitic arthropathy; ulcerative colitis; urticaria; usual interstitial pneumonia (UIP); uveitis; vasculitic diffuse lung disease; vasculitis; vernal conjunctivitis; viral retinitis; vitiligo; Vogt-Koyanagi-Harada syndrome (VKH syndrome); Wegener's granulomatosis; Wet macular degeneration; wound healing; *yersinia* and *salmonella* associated arthropathy.

The antibodies, and antibody portions of the invention can be used to treat humans suffering from autoimmune diseases, in particular those associated with inflammation, rheumatoid arthritis, osteoarthritis, psoriasis, multiple sclerosis, and other autoimmune diseases.

An antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention, or antigen binding portion thereof, can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition, e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Particular combinations are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the anti TNF-α antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-17, IL-18, IL-21, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Particular combinations of therapeutic agents may interfere at different points in the autoimmune and subsequent inflammatory cascade; particular examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF-α converting enzyme (TACE) inhibitors; similarly IL-1 inhibitors (Interleukin-1-converting enzyme inhibitors, IL-1RA etc.) may be effective for the same reason. Other combinations are with Interleukin 11. Yet other combinations are with other key players of the autoimmune response which may act in parallel to, dependently on or in concert with TNF-α function. Yet other combinations are with non-depleting anti-CD4 inhibitors. Yet other combinations are with antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNF-α or IL-1 (e.g., IRAK, NIK, IKK, p38 or MAP kinase inhibitors), IL-1β converting enzyme inhibitors, TNF-α converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SC10-469, VX-702, AMG-548, VX-740, Roflumilast, IC-485, CDC-801, and Mesopram. Particular combinations include methotrexate or leflunomide and in moderate or severe rheumatoid arthritis cases, cyclosporine.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

Example 1

Recombinant Anti-Human TNF-α Antibodies

Example 1.1

Construction and Expression of Recombinant Chimeric Anti-Human TNF-α Antibodies

The DNA encoding the heavy chain constant region of murine anti-human TNF-α monoclonal antibody MAK195 was replaced by a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al. (1991) *J. Immunol.* 147:2657-2662). The light chain constant region of each of these antibodies was replaced by a human kappa constant region. Full-length chimeric antibodies were transiently expressed in HEK293 cells by co-transfection of chimeric heavy and light chain cDNAs ligated into the pHybE expression plasmid. Cell supernatants containing recombinant chimeric antibody were purified by protein A sepharose chromatography and bound antibody was eluted by addition of acid buffer. Antibodies were neutralized and dialyzed into PBS.

The purified chimeric anti-human TNF-α monoclonal antibodies were then tested for their ability to bind the hTNF-α protein by ELISA to confirm antigen binding.

Example 1.2

Construction of CDR Grafted Anti-Human TNF-α Antibodies

By applying standard methods well known in the art, the CDR sequences of VH and VL chains of monoclonal antibody MAK195 (see Table 5 above) were grafted into different human heavy and light chain acceptor sequences.

Based on sequence VH and VL alignments with the VH and VL sequences of monoclonal antibody MAK195 of the present invention the following known human sequences were selected:

a) VH4-59 (IGHV4-59) and VH3-53 (IGHV3-53) as well as the joining sequences hJH4 for constructing heavy chain acceptor sequences
b) 1-39/O12 and 3-15/L2 as well as hJK2 for constructing light chain acceptor sequences By grafting the corresponding VH and VL CDRs of MAK195 into said acceptor sequences, the CDR-grafted, humanized, and modified VH and VL sequences were prepared (see also Table 6, above).

Example 1.3

Construction of Framework Back Mutations in CDR-Grafted Antibodies

To generate humanized antibody framework back mutations, mutations are introduced into the CDR-grafted antibody sequences as prepared according to Example 1.2, by de novo synthesis of the variable domain and/or using mutagenic primers and PCR, and methods well known in the art (see, e.g., WO 2007/042261; WO 99/54440; Traunecker et al. (1987) *EMBO J.*, 10(12):3655-9 and Lanzavecchia and Scheidegger (1987) *Eur. J. Immunol.*, 17(1):105-11. Different combinations of back mutations and other mutations are constructed for each of the CDR-grafts as follows. A summary of the proposed design versions of each humanized antibody is set forth below. Residue numbers for these mutations are based on the Kabat numbering system.

For heavy chains hMAK195VH.1z, one or more of the following Vernier and VH/VL interfacing residues were back mutated as follows: G27→F, I29→L, I37→V, I48→L, V67→L, V71→K, T73→N, N76→S, and F78→I.

Additional mutations include the following: Q1→E.

For heavy chains hMAK195VH.2z, one or more of the following Vernier and VH/VL interfacing residues are back mutated as follows: A24→V, F29→L, V48→L, F67→L, R71→K, S49→G, N76→S, and L78→I.

Additional mutations include the following: Q1→E, I12→V, and V29→F.

For light chain hMAK195Vk.1 one or more of the following Vernier and VH/VL interfacing residues are back mutated as follows: A43→S.

For light chain hMAK195Vk.2z one or more of the following Vernier and VH/VL interfacing residues are back mutated as follows: A43→S, I58→V.

Additional mutation include the following: V13→L, E70→D, and S80→P.

Example 1.4

Humanized Anti-hTNF-α Heavy and Light Chains Containing Framework Back Mutations

| SEQ ID No. | Protein region | Sequence<br>12345678901234567890123456789O |
|---|---|---|
| SEQ ID NO: 28 | hMAK195VH.1 | EVQLQESGPGLVKPSETLSLTCTVSGGSIS<br>DYGVNWIRQPPGKGLEWIGMIWGDGSTDYD<br>STLKSRVTISVDTSKNQFSLKLSSVTAADT<br>AVYYCAREWHHGPVAYWGQGTLVTVSS |
| SEQ ID NO: 29 | hMAK195VH.1a | EVQLQESGPGLVKPSETLSLTCTVSGFSLS<br>DYGVNWVRQAPGKGLEWLGMIWGDGSTDYD |

| SEQ ID No. | Protein region | Sequence<br>123456789012345678901234567890 |
|---|---|---|
| | | STLKSRLTISKDNSKSQISLKLSSVTAADT<br>AVYYCAREWHHGPVAYWGQGTLVTVSS |
| SEQ ID NO: 30 | hMAK195VH.1b | EVQLQESGPGLVKPSETLSLTCTVSGFSLS<br>DYGVNWIRQPPGKGLEWIGMIWGDGSTDYD<br>STLKSRVTISKDTSKNQFSLKLSSVTAADT<br>AVYYCAREWHHGPVAYWGQGTLVTVSS |
| SEQ ID NO: 31 | hMAK195VH.2 | EVQLVESGGGLVQPGGSLRLSCAASGFTFS<br>DYGVNWVRQAPGKGLEWVSMIWGDGSTDYD<br>STLKSRFTISRDNSKNTLYLQMNSLRAEDT<br>AVYYCAREWHHGPVAYWGQGTLVTVSS |
| SEQ ID NO: 32 | hMAK195VH.2a | EVQLVESGGGLVQPGGSLRLSCAVSGFTLS<br>DYGVNWVRQAPGKGLEWLGMIWGDGSTDYD<br>STLKSRLTISKDNSKSTIYLQMNSLRAEDT<br>AVYYCAREWHHGPVAYWGQGTLVTVSS |
| SEQ ID NO: 33 | hMAK195VH.2b | EVQLVESGGGLVQPGGSLRLSCAASGFTLS<br>DYGVNWVRQAPGKGLEWVSMIWGDGSTDYD<br>STLKSRFTISKDNSKNTLYLQMNSLRAEDT<br>AVYYCAREWHHGPVAYWGQGTLVTVSS |
| SEQ ID NO: 34 | hMAK195Vk.1a | DIQMTQSPSSLSASVGDRVTITCKASQAVS<br>SAVAWYQQKPGKSPKLLIYWASTRHTGVPS<br>RFSGSGSGTDFTLTISSLQPEDFAVYYCQQ<br>HYSTPFTFGQGTKLEIK |
| SEQ ID NO: 35 | hMAK195Vk.2 | EIVMTQSPATLSLSPGERATLSCKASQAVS<br>SAVAWYQQKPGQAPRLLIYWASTRHTGIPA<br>RFSGSGSGTDFTLTISSLQPEDFAVYYCQQ<br>HYSTPFTFGQGTKLEIK |
| SEQ ID NO: 36 | hMAK195Vk.2a | EIVMTQSPATLSLSPGERATLSCKASQAVS<br>SAVAWYQQKPGQSPRLLIYWASTRHTGVPA<br>RFSGSGSGTDFTLTISSLQPEDFAVYYCQQ<br>HYSTPFTFGQGTKLEIK |

Example 1.5

Humanized Anti-hTNF-α hMAK195 Antibody VH/VL Pairings

| Antibody Designation | VH | VL |
|---|---|---|
| AB240 | hMAK195VH.1 | hMAK195VL.1 |
| AB241 | hMAK195VH.1 | hMAK195VL.1a |
| AB242 | hMAK195VH.1 | hMAK195VL.2 |
| AB243 | hMAK195VH.1 | hMAK195VL.2a |
| AB244 | hMAK195VH.1a | hMAK195VL.1 |
| AB245 | hMAK195VH.1a | hMAK195VL.1a |
| AB246 | hMAK195VH.1a | hMAK195VL.2 |
| AB247 | hMAK195VH.1a | hMAK195VL.2a |
| AB248 | hMAK195VH.1b | hMAK195VL.1 |
| AB249 | hMAK195VH.1b | hMAK195VL.1a |
| AB250 | hMAK195VH.1b | hMAK195VL.2 |
| AB251 | hMAK195VH.1b | hMAK195VL.2a |
| AB252 | hMAK195VH.2 | hMAK195VL.1 |
| AB253 | hMAK195VH.2 | hMAK195VL.1a |
| AB254 | hMAK195VH.2 | hMAK195VL.2 |
| AB255 | hMAK195VH.2 | hMAK195VL.2a |
| AB256 | hMAK195VH.2a | hMAK195VL.1 |
| AB257 | hMAK195VH.2a | hMAK195VL.1a |
| AB258 | hMAK195VH.2a | hMAK195VL.2 |
| AB259 | hMAK195VH.2a | hMAK195VL.2a |
| AB260 | hMAK195VH.2b | hMAK195VL.1 |
| AB261 | hMAK195VH.2b | hMAK195VL.1a |
| AB262 | hMAK195VH.2b | hMAK195VL.2 |
| AB263 | hMAK195VH.2b | hMAK195VL.2a |

Example 1.6

Affinity Determination Using BIACORE Technology

TABLE 7

| Reagent Used in Biacore Analyses | | | |
|---|---|---|---|
| Antigen | Vendor Designation | Vendor | Catalog # |
| TNFα | Recombinant Human TNF-α/TNFSF1A | R&D systems | 210-TA |

BIACORE Methods:

The BIACORE assay (Biacore, Inc. Piscataway, N.J.) determines the affinity of antibodies with kinetic measurements of on-rate and off-rate constants. Binding of antibodies to a target antigen (for example, a purified recombinant target antigen) is determined by surface plasmon resonance-based measurements with a Biacore® 1000 or 3000 instrument (Biacore® AB, Uppsala, Sweden) using running HBS-EP (10 mM HEPES [pH 7.4], 150 mM NaCl, 3 mM EDTA, and 0.005% surfactant P20) at 25° C. All chemicals are obtained from Biacore® AB (Uppsala, Sweden) or otherwise from a different source as described in the text. For example, approximately 5000 RU of goat anti-mouse IgG, (Fcγ), fragment specific polyclonal antibody (Pierce Biotechnology Inc, Rockford, Ill., US) diluted in 10 mM sodium acetate (pH 4.5) is directly immobilized across a CM5 research grade biosensor chip using a standard amine coupling kit according to manufacturer's instructions and procedures at 25 μg/ml. Unreacted moieties on the biosensor surface are blocked with ethanolamine. Modified carboxymethyl dextran surface in flowcell 2 and 4 is used as a reaction surface. Unmodified carboxymethyl dextran without goat anti-mouse IgG in flow cell 1 and 3 is used as the reference surface. For kinetic analysis, rate equations derived from the 1:1 Langmuir binding model are fitted simultaneously to association and dissociation phases of all eight injections (using global fit analysis) with the use of Biaevaluation 4.0.1 software. Purified antibodies are diluted in HEPES-buffered saline for capture across goat anti-mouse IgG specific reaction surfaces. Antibodies to be captured as a ligand (25 μg/ml) are injected over reaction matrices at a flow rate of 5 μl/minute. The association and dissociation rate constants, $k_{on}$ ($M^{-1}s^{-1}$) and $k_{off}$ ($s^{-1}$), are determined under a continuous flow rate of 25 μl/minute. Rate constants are derived by making kinetic binding measurements at different antigen concentrations ranging from 10-200 nM. The equilibrium dissociation constant (M) of the reaction between antibodies and the target antigen is then calculated from the kinetic rate constants by the following formula: $K_D=k_{off}/k_{on}$. Binding is recorded as a function of time and kinetic rate constants are calculated. In this assay, on-rates as fast as $10^6$ $M^{-1}s^{-1}$ and off-rates as slow as $10^{-6}$ $s^{-1}$ can be measured.

were washed with PBS, counted and resuspended at 1E6 cells/mL in assay media containing 4 μg/mL actinomycin D. The cells were seeded in a 96-well plate (Costar#3599) at a volume of 100 pt and 5E4 cells/well. The antibodies and control IgG were diluted to a 4× concentration in assay media and serial 1:4 dilutions were performed. The huTNF-α was diluted to 400 μg/mL in assay media. Antibody sample (200 μL) was added to the huTNF-α (200 μL) in a 1:2 dilution scheme and allowed to incubate for 0.5 hour at room temperature.

The antibody/human TNF-α solution was added to the plated cells at 100 pt for a final concentration of 100 pg/mL huTNF-α and 150 nM-0.0001 nM antibody. The plates were incubated for 20 hours at 37° C., 5% $CO_2$. To quantitate viability, 100 μL was removed from the wells and 10 μL of WST-1 reagent (Roche cat#11644807001) was added. Plates were incubated under assay conditions for 3.5 hours. The plates were read at OD 420-600 nm on a Spectromax 190 ELISA plate reader. An average EC50 from several assays is included in Table 9.

TABLE 8

BIACORE Analysis of Anti-hTNF-α Antibodies

| Antibody Designation | VH | VL | $k_{on}$ (M-1s-1) | $k_{off}$ (s-1) | $k_D$ (M) |
|---|---|---|---|---|---|
| AB240 | hMAK195VH.1 | hMAK195VL.1 | 1.64E+06 | 2.28E-03 | 1.40E-09 |
| AB241 | hMAK195VH.1 | hMAK195VL.1a | 2.27E+06 | 1.30E-03 | 5.73E-10 |
| AB242 | hMAK195VH.1 | hMAK195VL.2 | 1.79E+06 | 1.42E-03 | 7.96E-10 |
| AB243 | hMAK195VH.1 | hMAK195VL.2a | 1.72E+06 | 2.70E-03 | 1.62E-09 |
| AB244 | hMAK195VH.1a | hMAK195VL.1 | 3.80E+06 | 3.35E-04 | 8.91E-11 |
| AB245 | hMAK195VH.1a | hMAK195VL.1a | 3.32E+06 | 3.30E-04 | 9.94E-11 |
| AB246 | hMAK195VH.1a | hMAK195VL.2 | 2.61E+06 | 1.19E-04 | 4.58E-11 |
| AB247 | hMAK195VH.1a | hMAK195VL.2a | 2.62E+06 | 2.60E-04 | 9.96E-11 |
| AB248 | hMAK195VH.1b | hMAK195VL.1 | 1.82E+06 | 3.16E-04 | 1.74E-10 |
| A3249 | hMAK195VH.1b | hMAK195VL.1a | 2.04E+06 | 3.15E-04 | 1.56E-10 |
| AB250 | hMAK195VH.1b | hMAK195VL.2 | 2.00E+06 | 3.56E-04 | 1.79E-10 |
| AB251 | hMAK195VH.1b | hMAK195VL.2a | 1.71E+06 | 4.25E-04 | 2.50E-10 |
| AB252 | hMAK195VH.2 | hMAK195VL.1 | 2.92E+06 | 2.52E-04 | 8.66E-11 |
| AB253 | hMAK195VH.2 | hMAK195VL.1a | 3.02E+06 | 2.21E-04 | 7.33E-11 |
| AB254 | hMAK195VH.2 | hMAK195VL.2 | 2.40E+06 | 2.87E-04 | 1.20E-10 |
| AB255 | hMAK195VH.2 | hMAK195VL.2a | 2.62E+06 | 3.84E-04 | 1.48E-10 |
| AB256 | hMAK195VH.2a | hMAK195VL.1 | 3.54E+06 | 1.77E-04 | 5.05E-11 |
| AB257 | hMAK195VH.2a | hMAK195VL.1a | 3.56E+06 | 2.17E-04 | 6.20E-11 |
| AB258 | hMAK195VH.2a | hMAK195VL.2 | 3.04E+06 | 2.44E-04 | 8.16E-11 |
| AB259 | hMAK195VH.2a | hMAK195VL.2a | 3.00E+06 | 2.03E-04 | 6.77E-11 |
| AB260 | hMAK195VH.2b | hMAK195VL.1 | 2.27E+06 | 2.30E-04 | 1.01E-10 |
| AB261 | hMAK195VH.2b | hMAK195VL.1a | 2.36E+06 | 2.85E-04 | 1.22E-10 |
| AB262 | hMAK195VH.2b | hMAK195VL.2 | 2.14E+06 | 2.90E-04 | 1.36E-10 |
| AB263 | hMAK195VH.2b | hMAK195VL.2a | 1.61E+06 | 2.73E-04 | 1.69E-10 |

Binding of all humanized constructs characterized by Biacore technology was maintained and comparable to that of the murine parental antibody.

Example 1.7

Neutralization of Human TNF-α

L929 cells were grown to a semi-confluent density and harvested using 0.25% trypsin (Gibco#25300). The cells

TABLE 9

Human TNF-α Neutralization Assay with Humanized anti-hTNF-α Antibodies

| Antibody Designation | VH | VL | TNF-α neutralization assay $IC_{50}$ (nM) |
|---|---|---|---|
| AB240 | hMAK195VH.1 | hMAK195VL.1 | 14.190 |
| AB241 | hMAK195VH.1 | hMAK195VL.1a | 5.325 |
| AB242 | hMAK195VH.1 | hMAK195VL.2 | 25.150 |
| AB243 | hMAK195VH.1 | hMAK195VL.2a | 50.710 |
| AB244 | hMAK195VH.1a | hMAK195VL.1 | 0.155 |
| AB245 | hMAK195VH.1a | hMAK195VL.1a | 0.072 |
| AB246 | hMAK195VH.1a | hMAK195VL.2 | 0.099 |

TABLE 9-continued

Human TNF-α Neutralization Assay with Humanized anti-hTNF-α Antibodies

| Antibody Designation | VH | VL | TNF-α neutralization assay $IC_{50}$ (nM) |
|---|---|---|---|
| AB247 | hMAK195VH.1a | hMAK195VL.2a | 0.186 |
| AB248 | hMAK195VH.1b | hMAK195VL.1 | 0.213 |
| AB249 | hMAK195VH.1b | hMAK195VL.1a | 0.245 |
| AB250 | hMAK195VH.1b | hMAK195VL.2 | 0.301 |
| AB251 | hMAK195VH.1b | hMAK195VL.2a | 0.350 |
| AB252 | hMAK195VH.2 | hMAK195VL.1 | 0.222 |
| AB253 | hMAK195VH.2 | hMAK195VL.1a | 0.279 |
| AB254 | hMAK195VH.2 | hMAK195VL.2 | 0.799 |
| AB255 | hMAK195VH.2 | hMAK195VL.2a | 0.477 |
| AB256 | hMAK195VH.2a | hMAK195VL.1 | 0.058 |
| AB257 | hMAK195VH.2a | hMAK195VL.1a | 0.077 |
| AB258 | hMAK195VH.2a | hMAK195VL.2 | 0.078 |
| AB259 | hMAK195VH.2a | hMAK195VL.2a | 0.071 |
| AB260 | hMAK195VH.2b | hMAK195VL.1 | 0.093 |
| AB261 | hMAK195VH.2b | hMAK195VL.1a | 0.187 |
| AB262 | hMAK195VH.2b | hMAK195VL.2 | 0.218 |
| AB263 | hMAK195VH.2b | hMAK195VL.2a | 0.193 |

All anti-hTNF-α antibodies showed neutralization in the TNF-α neutralization assay.

Example 1.8

Physicochemical and In Vitro Stability Analysis of Humanized Monoclonal Antibodies Size Exclusion Chromatography Antibodies were diluted to 2.5 mg/mL with water and 20 mL analyzed on a Shimadzu HPLC system using a TSK gel G3000 SWXL column (Tosoh Bioscience, cat# k5539-05k). Samples were eluted from the column with 211 mM sodium sulfate, 92 mM sodium phosphate, pH 7.0, at a flow rate of 0.3 mL/minutes. The HPLC system operating conditions were the following:

Mobile phase: 211 mM $Na_2SO_4$, 92 mM $Na_2HPO_4$*$7H_2O$, pH 7.0
Gradient: Isocratic
Flow rate: 0.3 mL/minute
Detector wavelength: 280 nm
Autosampler cooler temp: 4° C.
Column oven temperature: ambient
Run time: 50 minutes Table 10 contains purity data of antibody constructs expressed as percent monomer (unaggregated protein of the expected molecular weight) as determined by the above protocol.

TABLE 10

Purity of anti-hTNF-α Antibodies as Determined by Size Exclusion Chromatography

| Antibody Designation | VH | VL | % monomer (purity) |
|---|---|---|---|
| AB240 | hMAK195VH.1 | hMAK195VL.1 | 88.6 |
| AB241 | hMAK195VH.1 | hMAK195VL.1a | 93.4 |
| AB242 | hMAK195VH.1 | hMAK195VL.2 | 89.8 |
| AB243 | hMAK195VH.1 | hMAK195VL.2a | 92.2 |
| AB244 | hMAK195VH.1a | hMAK195VL.1 | 100 |
| AB245 | hMAK195VH.1a | hMAK195VL.1a | 99 |
| AB246 | hMAK195VH.1a | hMAK195VL.2 | 98.8 |
| AB247 | hMAK195VH.1a | hMAK195VL.2a | 99 |
| AB248 | hMAK195VH.1b | hMAK195VL.1 | 93.5 |
| AB249 | hMAK195VH.1b | hMAK195VL.1a | 96 |
| AB250 | hMAK195VH.1b | hMAK195VL.2 | 93.8 |
| AB251 | hMAK195VH.1b | hMAK195VL.2a | 95.4 |
| AB252 | hMAK195VH.2 | hMAK195VL.1 | 98.4 |
| AB253 | hMAK195VH.2 | hMAK195VL.1a | 98.6 |
| AB254 | hMAK195VH.2 | hMAK195VL.2 | 97.5 |
| AB255 | hMAK195VH.2 | hMAK195VL.2a | 97.7 |
| AB256 | hMAK195VH.2a | hMAK195VL.1 | 95.7 |
| AB257 | hMAK195VH.2a | hMAK195VL.1a | 96.7 |
| AB258 | hMAK195VH.2a | hMAK195VL.2 | 95.6 |
| AB259 | hMAK195VH.2a | hMAK195VL.2a | 96.6 |
| AB260 | hMAK195VH.2b | hMAK195VL.1 | 99.1 |
| AB261 | hMAK195VH.2b | hMAK195VL.1a | 100 |
| AB262 | hMAK195VH.2b | hMAK195VL.2 | 98.6 |
| AB263 | hMAK195VH.2b | hMAK195VL.2a | 98.9 |

Anti-hTNF-α antibodies showed an excellent SEC profile with most showing >95% monomer.

Sodium Dodecyl Sulfate-Polyacrylamide Gel Electrophoresis (SDS-PAGE)

Antibodies are analyzed by sodium dodecyl sulfate-polyacrylamide gel electrophoresis (SDS-PAGE) under both reducing and non-reducing conditions. Adalimumab lot AFP04C is used as a control. For reducing conditions, the samples are mixed 1:1 with 2× tris glycine SDS-PAGE sample buffer (Invitrogen, cat# LC2676, lot#1323208) with 100 mM DTT, and heated at 60° C. for 30 minutes. For non-reducing conditions, the samples are mixed 1:1 with sample buffer and heated at 100° C. for 5 minutes. The reduced samples (10 mg per lane) are loaded on a 12% pre-cast tris-glycine gel (Invitrogen, cat# EC6005box, lot#6111021), and the non-reduced samples (10 mg per lane) are loaded on an 8%-16% pre-cast tris-glycine gel (Invitrogen, cat#EC6045box, lot#6111021). SeeBlue Plus 2 (Invitrogen, cat#LC5925, lot#1351542) is used as a molecular weight marker. The gels are run in a XCell SureLock mini cell gel box (Invitrogen, cat# EI0001) and the proteins are separated by first applying a voltage of 75 to stack the samples in the gel, followed by a constant voltage of 125 until the dye front reached the bottom of the gel. The running buffer used is 1× tris glycine SDS buffer, prepared from a 10× tris glycine SDS buffer (ABC, MPS-79-080106)). The gels are stained overnight with colloidal blue stain (Invitrogen cat#46-7015, 46-7016) and destained with Milli-Q water until the background is clear. The stained gels are then scanned using an Epson Expression scanner (model 1680, S/N DASX003641).

Sedimentation Velocity Analysis

Antibodies are loaded into the sample chamber of each of three standard two-sector carbon epon centerpieces. These centerpieces have a 1.2 cm optical path length and are built with sapphire windows. PBS is used for a reference buffer and each chamber contained 140 μL. All samples are examined simultaneously using a 4-hole (AN-60Ti) rotor in a Beckman ProteomeLab XL-I analytical ultracentrifuge (serial # PL106C01).

Run conditions are programmed and centrifuge control is performed using ProteomeLab (v5.6). The samples and rotor are allowed to thermally equilibrate for one hour prior to analysis (20.0±0.1° C.). Confirmation of proper cell loading is performed at 3000 rpm and a single scan is recorded for each cell. The sedimentation velocity conditions are the following:

Sample Cell Volume: 420 mL
Reference Cell Volume: 420 mL
Temperature: 20° C.
Rotor Speed: 35,000 rpm
Time: 8:00 hours
UV Wavelength: 280 nm
Radial Step Size: 0.003 cm
Data Collection One data point per step without signal averaging.
Total Number of Scans: 100

LC-MS Molecular Weight Measurement of Intact Antibodies

Molecular weights of intact antibodies are analyzed by LC-MS. Each antibody is diluted to approximately 1 mg/mL with water. An 1100 HPLC (Agilent) system with a protein microtrap (Michrom Bioresources, Inc, cat#004/25109/03) is used to desalt and introduce 5 mg of the sample into an API QSTAR Pulsar i mass spectrometer (Applied Biosystems). A short gradient is used to elute the samples. The gradient is run with mobile phase A (0.08% FA, 0.02% TFA in HPLC water) and mobile phase B (0.08% FA and 0.02% TFA in acetonitrile) at a flow rate of 50 mL/minute. The mass spectrometer is operated at 4.5 kvolts spray voltage with a scan range from 2000 to 3500 mass to charge ratio.

LC-MS Molecular Weight Measurement of Antibody Light and Heavy Chains

Molecular weight measurement of antibody light chains (LC), heavy chains (HC) and deglycosylated HC are analyzed by LC-MS. Antibody is diluted to 1 mg/mL with water and the sample is reduced to LC and HC with a final concentration of 10 mM DTT for 30 minutes at 37° C. To deglycosylate the antibody, 100 mg of the antibody is incubated with 2 mL of PNGase F, 5 mL of 10% N-octylglucoside in a total volume of 100 mL overnight at 37° C. After deglycosylation the sample is reduced with a final concentration of 10 mM DTT for 30 minutes at 37° C. An Agilent 1100 HPLC system with a C4 column (Vydac, cat#214TP5115, S/N 060206537204069) is used to desalt and introduce the sample (5 mg) into an API QSTAR Pulsar mass spectrometer (Applied Biosystems). A short gradient is used to elute the sample. The gradient is run with mobile phase A (0.08% FA, 0.02% TFA in HPLC water) and mobile phase B (0.08% FA and 0.02% TFA in acetonitrile) at a flow rate of 50 mL/minute. The mass spectrometer is operated at 4.5 kvolts spray voltage with a scan range from 800 to 3500 mass to charge ratio.

Peptide Mapping

Antibody is denatured for 15 minutes at room temperature with a final concentration of 6 M guanidine hydrochloride in 75 mM ammonium bicarbonate. The denatured samples are reduced with a final concentration of 10 mM DTT at 37° C. for 60 minutes, followed by alkylation with 50 mM iodoacetic acid (IAA) in the dark at 37° C. for 30 minutes. Following alkylation, the sample is dialyzed overnight against four liters of 10 mM ammonium bicarbonate at 4° C. The dialyzed sample is diluted to 1 mg/mL with 10 mM ammonium bicarbonate, pH 7.8 and 100 mg of antibody is either digested with trypsin (Promega, cat# V5111) or Lys-C (Roche, cat#11 047 825 001) at a 1:20 (w/w) trypsin/Lys-C:antibody ratio at 37° C. for 4 hrs. Digests are quenched with 1 mL of 1 N HCl. For peptide mapping with mass spectrometer detection, 40 mL of the digests are separated by reverse phase high performance liquid chromatography (RPHPLC) on a C18 column (Vydac, cat#218TP51, S/N NE9606 10.3.5) with an Agilent 1100 HPLC system. The peptide separation is run with a gradient using mobile phase A (0.02% TFA and 0.08% FA in HPLC grade water) and mobile phase B (0.02% TFA and 0.08% FA in acetonitrile) at a flow rate of 50 mL/minutes. The API QSTAR Pulsar i mass spectrometer is operated in positive mode at 4.5 kvolts spray voltage and a scan range from 800 to 2500 mass to charge ratio.

Disulfide Bond Mapping

To denature the antibody, 100 mL of the antibody is mixed with 300 mL of 8 M guanidine HCl in 100 mM ammonium bicarbonate. The pH is checked to ensure that it is between 7 and 8 and the samples are denatured for 15 minutes at room temperature in a final concentration of 6 M guanidine HCl. A portion of the denatured sample (100 mL) is diluted to 600 mL with Milli-Q water to give a final guanidine-HCl concentration of 1 M. The sample (220 mg) is digested with either trypsin (Promega, cat #V5111, lot#22265901) or Lys-C (Roche, cat#11047825001, lot#12808000) at a 1:50 trypsin or 1:50 Lys-C: antibody (w/w) ratios (4.4 mg enzyme: 220 mg sample) at 37° C. for approximately 16 hours. An additional 5 mg of trypsin or Lys-C is added to the samples and digestion is allowed to proceed for an additional 2 hours at 37° C. Digestions are stopped by adding 1 mL of TFA to each sample. Digested samples are separated by RPHPLC using a C18 column (Vydac, cat#218TP51 S/N NE020630-4-1A) on an Agilent HPLC system. The separation is run with the same gradient used for peptide mapping using mobile phase A (0.02% TFA and 0.08% FA in HPLC grade water) and mobile phase B (0.02% TFA and 0.08% FA in acetonitrile) at a flow rate of 50 mL/minute. The HPLC operating conditions are the same as those used for peptide mapping. The API QSTAR Pulsar i mass spectrometer is operated in positive mode at 4.5 kvolts spray voltage and a scan range from 800 to 2500 mass-to-charge ratio. Disulfide bonds are assigned by matching the observed MWs of peptides with the predicted MWs of tryptic or Lys-C peptides linked by disulfide bonds.

Free Sulfhydryl Determination

The method used to quantify free cysteines in an antibody is based on the reaction of Ellman's reagent, 5,5'-dithio-bis (2-nitrobenzoic acid) (DTNB), with sulfhydryl groups (SH) which gives rise to a characteristic chromophoric product, 5-thio-(2-nitrobenzoic acid) (TNB). The reaction is illustrated in the formula:

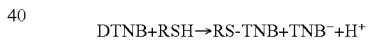

$$DTNB + RSH \rightarrow RS\text{-}TNB + TNB^- + H^+$$

The absorbance of the $TNB^-$ is measured at 412 nm using a Cary 50 spectrophotometer. An absorbance curve is plotted using dilutions of 2-mercaptoethanol (β-ME) as the free SH standard and the concentrations of the free sulfhydryl groups in the protein are determined from absorbance at 412 nm of the sample.

The β-ME standard stock is prepared by a serial dilution of 14.2 M β-ME with HPLC grade water to a final concentration of 0.142 mM. Then standards in triplicate for each concentration are prepared. Antibody is concentrated to 10 mg/mL using an amicon ultra 10,000 MWCO centrifugal filter (Millipore, cat# UFC801096, lot# L3KN5251) and the buffer is changed to the formulation buffer used for adalimumab (5.57 mM sodium phosphate monobasic, 8.69 mM sodium phosphate dibasic, 106.69 mM NaCl, 1.07 mM sodium citrate, 6.45 mM citric acid, 66.68 mM mannitol, pH 5.2, 0.1% (w/v) Tween®). The samples are mixed on a shaker at room temperature for 20 minutes. Then 180 mL of 100 mM Tris buffer, pH 8.1 is added to each sample and standard followed by the addition of 300 mL of 2 mM DTNB in 10 mM phosphate buffer, pH 8.1. After thorough mixing, the samples and standards are measured for absorption at 412 nm on a Cary 50 spectrophotometer. The standard curve is obtained by plotting the amount of free SH and $OD_{412}$ nm of the β-ME standards. Free SH content of samples are calculated based on this curve after subtraction of the blank.

Weak Cation Exchange Chromatography

Antibody is diluted to 1 mg/mL with 10 mM sodium phosphate, pH 6.0. Charge heterogeneity is analyzed using a Shimadzu HPLC system with a WCX-10 ProPac analytical column (Dionex, cat#054993, S/N 02722). The samples are loaded on the column in 80% mobile phase A (10 mM sodium phosphate, pH 6.0) and 20% mobile phase B (10 mM sodium phosphate, 500 mM NaCl, pH 6.0) and eluted at a flow rate of 1.0 mL/minute.

Oligosaccharide Profiling

Oligosaccharides released after PNGase F treatment of antibody are derivatized with 2-aminobenzamide (2-AB) labeling reagent. The fluorescent-labeled oligosaccharides are separated by normal phase high performance liquid chromatography (NPHPLC) and the different forms of oligosaccharides are characterized based on retention time comparison with known standards.

The antibody is first digested with PNGase F to cleave N-linked oligosaccharides from the Fc portion of the heavy chain. The antibody (200 mg) is placed in a 500 mL Eppendorf tube along with 2 mL PNGase F and 3 mL of 10% N-octylglucoside. Phosphate buffered saline is added to bring the final volume to 60 mL. The sample is incubated overnight at 37° C. in an Eppendorf thermomixer set at 700 RPM. Adalimumab lot AFP04C is also digested with PNGase F as a control.

After PNGase F treatment, the samples are incubated at 95° C. for 5 minutes in an Eppendorf thermomixer set at 750 RPM to precipitate out the proteins, then the samples are placed in an Eppendorf centrifuge for 2 minutes at 10,000 RPM to spin down the precipitated proteins. The supernatant containing the oligosaccharides are transferred to a 500 mL Eppendorf tube and dried in a speed-vac at 65° C.

The oligosaccharides are labeled with 2AB using a 2AB labeling kit purchased from Prozyme (cat# GKK-404, lot#132026). The labeling reagent is prepared according to the manufacturer's instructions. Acetic acid (150 mL, provided in kit) is added to the DMSO vial (provided in kit) and mixed by pipeting the solution up and down several times. The acetic acid/DMSO mixture (100 mL) is transferred to a vial of 2-AB dye (just prior to use) and mixed until the dye is fully dissolved. The dye solution is then added to a vial of reductant (provided in kit) and mixed well (labeling reagent). The labeling reagent (5 mL) is added to each dried oligosaccharide sample vial, and mixed thoroughly. The reaction vials are placed in an Eppendorf thermomixer set at 65° C. and 700-800 RPM for 2 hours of reaction.

After the labeling reaction, the excess fluorescent dye is removed using GlycoClean S Cartridges from Prozyme (cat# GKI-4726). Prior to adding the samples, the cartridges are washed with 1 mL of Milli-Q water followed with 5 washes of 1 mL 30% acetic acid solution. Just prior to adding the samples, 1 mL of acetonitrile (Burdick and Jackson, cat# AH015-4) is added to the cartridges.

After all of the acetonitrile passed through the cartridge, the sample is spotted onto the center of the freshly washed disc and allowed to adsorb onto the disc for 10 minutes. The disc is washed with 1 mL of acetonitrile followed by five washes of 1 mL of 96% acetonitrile. The cartridges are placed over a 1.5 mL Eppendorf tube and the 2-AB labeled oligosaccharides are eluted with 3 washes (400 mL each wash) of Milli-Q water.

The oligosaccharides are separated using a Glycosep N HPLC (cat# GKI-4728) column connected to a Shimadzu HPLC system. The Shimadzu HPLC system consisted of a system controller, degasser, binary pumps, autosampler with a sample cooler, and a fluorescent detector.

Stability at Elevated Temperatures

The final concentration of the antibodies is adjusted to 2 mg/mL with the appropriate buffers, surfactants, stabilizers, and/or sugars. The antibody solutions are then filter sterilized and 0.25 mL aliquots are prepared under sterile conditions. The aliquots are left at either –80° C., 5° C., 25° C., or 40° C. for 1, 2 or 3 weeks. At the end of the incubation period, the samples are analyzed by size exclusion chromatography and SDS-PAGE.

The stability samples are analyzed by SDS-PAGE under both reducing and non-reducing conditions. The procedure used is the same as described herein. The gels are stained overnight with colloidal blue stain (Invitrogen cat#46-7015, 46-7016) and destained with Milli-Q water until the background is clear. The stained gels are then scanned using an Epson Expression scanner (model 1680, S/N DASX003641). To obtain more sensitivity, the same gels are silver stained using silver staining kit (Owl Scientific, Gel Company, San Francisco, Calif. US) and the recommended procedures given by the manufacturer is used.

Example 1.9

Transfection and Expression in HEK 293-6E Cells

The anti-hTNF-α antibody vector constructs were transfected into 293 cells for production of protein. The 293 transient transfection procedure used is a modification of the methods published in Durocher et al. (2002) *Nucl. Acids Res.* 30(2e9):1-9 and Pham et al. (2005) *Biotech. Bioeng.* 90(3): 332-44. Reagents that were used in the transfection included:

HEK 293-6E cells (human embryonic kidney cell line stably expressing EBNA1; obtained from National Research Council Canada) cultured in disposable Erlenmeyer flasks in a humidified incubator set at 130 rpm, 37° C. and 5% $CO_2$.

Culture medium: FreeStyle 293 Expression Medium (Invitrogen 12338-018) plus 25 µg/mL Geneticin (G418) (Invitrogen 10131-027) and 0.1% Pluronic F-68 (Invitrogen 24040-032).

Transfection medium: FreeStyle 293 Expression Medium plus 10 mM HEPES (Invitrogen 15630-080).

Polyethylenimine (PEI) stock: 1 mg/mL sterile stock solution, pH 7.0, prepared with linear 25 kDa PEI (Polysciences) and stored at less than –15° C.

Tryptone Feed Medium: 5% w/v sterile stock of Tryptone N1 (Organotechnie, 19554) in FreeStyle 293 Expression Medium.

Cell preparation for transfection: Approximately 2-4 hours prior to transfection, HEK 293-6E cells were harvested by centrifugation and resuspended in culture medium at a cell density of approximately 1 million viable cells per mL. For each transfection, 40 mL of the cell suspension were transferred into a disposable 250-mL Erlenmeyer flask and incubated for 2-4 hours.

Transfection: The transfection medium and PEI stock were prewarmed to room temperature (RT). For each transfection, 25 µg of plasmid DNA and 50 µg of polyethylenimine (PEI) were combined in 5 mL of transfection medium and incubated for 15-20 minutes at RT to allow the DNA:PEI complexes to form. For the BR3-Ig transfections, 25 µg of BR3-Ig plasmid was used per transfection. Each 5-mL DNA:PEI complex mixture was added to a 40-mL culture prepared previously and returned to the humidified incubator set at 130 rpm, 37° C. and 5% $CO_2$. After 20-28 hours, 5 mL of Tryptone Feed Medium was added to each transfection and the cultures were continued for six days.

Table 11 contains the yield data for parent antibodies expressed as milligrams per liter in HEK 293-6E cells.

TABLE 11

Transient Expression in Yields of anti-hTNF-α Antibodies in HEK 293-6E Cells

| Antibody Designation | VH | VL | Expression yield (mg/L) |
|---|---|---|---|
| AB240 | hMAK195VH.1 | hMAK195VL.1 | 101.4 |
| AB241 | hMAK195VH.1 | hMAK195VL.1a | 100.4 |
| AB242 | hMAK195VH.1 | hMAK195VL.2 | 66.4 |
| AB243 | hMAK195VH.1 | hMAK195VL.2a | 89 |
| AB244 | hMAK195VH.1a | hMAK195VL.1 | 87.6 |
| AB245 | hMAK195VH.1a | hMAK195VL.1a | 83.8 |
| AB246 | hMAK195VH.1a | hMAK195VL.2 | 58.6 |
| AB247 | hMAK195VH.1a | hMAK195VL.2a | 73 |
| AB248 | hMAK195VH.1b | hMAK195VL.1 | 83.2 |
| AB249 | hMAK195VH.1b | hMAK195VL.1a | 89 |
| AB250 | hMAK195VH.1b | hMAK195VL.2 | 65.4 |
| AB251 | hMAK195VH.1b | hMAK195VL.2a | 77.2 |
| AB252 | hMAK195VH.2 | hMAK195VL.1 | 21.4 |
| AB253 | hMAK195VH.2 | hMAK195VL.1a | 52 |
| AB254 | hMAK195VH.2 | hMAK195VL.2 | 5.8 |
| AB255 | hMAK195VH.2 | hMAK195VL.2a | 12.56 |
| AB256 | hMAK195VH.2a | hMAK195VL.1 | 99.6 |
| AB257 | hMAK195VH.2a | hMAK195VL.1a | 102.8 |
| AB258 | hMAK195VH.2a | hMAK195VL.2 | 62 |
| AB259 | hMAK195VH.2a | hMAK195VL.2a | 78.2 |
| AB260 | hMAK195VH.2b | hMAK195VL.1 | 69.4 |
| AB261 | hMAK195VH.2b | hMAK195VL.1a | 98.4 |
| AB262 | hMAK195VH.2b | hMAK195VL.2 | 30.8 |
| AB263 | hMAK195VH.2b | hMAK195VL.2a | 49.2 |

All antibodies expressed well in HEK 293-6E cells. In most cases >50 mg/L purified antibody could be obtained easily from supernatants of HEK 293-6E cells.

INCORPORATION BY REFERENCE

The present invention incorporates by reference in their entirety techniques well known in the field of molecular biology and drug delivery. These techniques include, but are not limited to, techniques described in the following publications: Ausubel et al. (eds.), *Current Protocols in Molecular Biology*, John Wiley & Sons, NY (1993); Ausubel, F. M. et al. eds., *Short Protocols In Molecular Biology* (4th Ed. 1999) John Wiley & Sons, NY. (ISBN 0-471-32938-X). *Controlled Drug Bioavailability Drug Product Design and Performance*, Smolen and Ball (eds.), Wiley, New York (1984); Giege et al., Chapter 1, In *Crystallization of Nucleic Acids and Proteins, A Practical Approach, 2nd ed.*, (Ducruix and Giege, eds.) (Oxford University Press, New York, 1999) pp. 1-16; Goodson, J. M., Chapter 6, In *Medical Applications of Controlled Release, Vol. II, Applications and Evaluation*, (Langer and Wise, eds.) (CRC Press, Inc., Boca Raton, 1984), pp. 115-138; Hammerling et al., eds., "Monoclonal Antibodies and T-Cell Hybridomas," In *Research Monographs in Immunology*, vol. 3 (J. L. Turk, General Editor) (Elsevier, N.Y., 1981), pp. 563-587; Harlow et al., *Antibodies: A Laboratory Manual*, (Cold Spring Harbor Laboratory Press, 2nd ed. 1988); Kabat et al., *Sequences of Proteins of Immunological Interest* (National Institutes of Health, Bethesda, Md. (1987); Kabat, E. A., et al. (1991) *Sequences of Proteins of Immunological Interest*, Fifth Edition, U.S. Department of Health and Human Services, NIH Publication No. 91-3242; Kontermann and Dübel, eds., *Antibody Engineering* (2001) Springer-Verlag. New York. 790 pp. (ISBN 3-540-41354-5); Kriegler, *Gene Transfer and Expression, A Laboratory Manual*, Stockton Press, NY (1990); Lu and Weiner eds., *Cloning and Expression Vectors for Gene Function Analysis* (2001) Bio-Techniques Press. Westborough, Mass. 298 pp. (ISBN 1-881299-21-X); Goodson, J. M., *Medical Applications of Controlled Release*, (Langer and Wise, eds.) (CRC Press, Boca Raton, 1974); Old and Primrose, *Principles of Gene Manipulation: An Introduction To Genetic Engineering* (3d Ed. 1985) Blackwell Scientific Publications, Boston; *Studies in Microbiology*, V.2:409 pp. (ISBN 0-632-01318-4); Sambrook, J. et al., *Molecular Cloning: A Laboratory Manual* (2d Ed. 1989) Cold Spring Harbor Laboratory Press, NY. Vols. 1-3 (ISBN 0-87969-309-6); *Sustained and Controlled Release Drug Delivery Systems*, (J. R. Robinson, ed.) (Marcel Dekker, Inc., New York, 1978); Winnacker, E. L. *From Genes To Clones: Introduction To Gene Technology* (1987) VCH Publishers, N.Y. (translated by Horst Ibelgaufts), 634 pp. (ISBN 0-89573-614-4).

The contents of all cited references (including literature references, patents, patent applications, and websites) that are cited throughout this application are hereby expressly incorporated by reference in their entirety, as are the references cited therein. The practice of the present invention will employ, unless otherwise indicated, conventional techniques of immunology, molecular biology and cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

We claim:

1. A humanized binding protein or antigen binding fragment thereof comprising an antigen binding domain capable of binding human tumor necrosis factor-alpha (TNF-α), the antigen binding domain comprising a heavy chain variable region (VH) and a light chain variable region (VL), wherein the VH region comprises an amino acid sequence selected from the group consisting of SEQ ID NOs: 29, 30, 31, 32, and 33, and the VL region comprises an amino acid sequence selected from the group consisting of SEQ ID NOs: 34, 35, and 36.

2. The humanized binding protein or antigen binding fragment thereof of claim 1, wherein the binding protein or antigen binding fragment thereof inhibits a biological function of human TNF-α.

3. The humanized binding protein or antigen binding fragment thereof of claim 1, wherein the binding protein or antigen binding fragment thereof neutralizes human TNF-α.

4. The humanized binding protein or antigen binding fragment thereof of claim 1, wherein the binding protein or antigen binding fragment thereof diminishes the ability of human TNF-α to bind to its receptor.

5. The humanized binding protein or antigen binding fragment thereof of claim 4, wherein the binding protein or antigen binding fragment thereof diminishes the ability of pro-human TNF-α, mature-human TNF-α, or truncated-human TNF-α to bind to its receptor.

6. The humanized binding protein or antigen binding fragment thereof of claim 1, wherein the binding protein or antigen binding fragment thereof reduces one or more of an activity selected from the group consisting of TNF-α-dependent cytokine production; TNF-α-dependent cell killing;

TNF-α-dependent inflammation; TNF-α-dependent bone erosion; and TNF-α-dependent cartilage damage.

7. The humanized binding protein or antigen binding fragment thereof of claim 1, wherein the binding protein or antigen binding fragment thereof comprises a constant domain selected from the group consisting of a heavy chain immunoglobulin constant domain of a human IgM constant domain, a human IgG1 constant domain, a human IgG2 constant domain, a human IgG3 constant domain, a human IgG4 constant domain, a human IgA constant domain, or a human IgE constant domain.

8. The humanized binding protein or antigen binding fragment thereof of claim 7, wherein the heavy chain immunoglobulin constant domain is a human IgG1 constant domain.

9. The humanized binding protein or antigen binding fragment thereof of claim 1 or 7, wherein the binding protein or antigen binding fragment thereof further comprises a light chain immunoglobulin constant domain selected from the group consisting of a human Ig kappa constant domain and a human Ig lambda constant domain.

10. The humanized binding protein or antigen binding fragment thereof of claim 8, wherein the human IgG1 constant domain comprises an amino acid sequence of selected from the group consisting of SEQ ID NO:2 Of and SEQ ID NO:3.

11. The humanized binding protein or antigen binding fragment thereof of claim 9, wherein the human Ig kappa constant domain comprises an amino acid sequence of SEQ ID NO:4, or the human Ig lambda constant domain comprises an amino acid sequence of SEQ ID NO:5.

12. The humanized binding protein or antigen binding fragment thereof of claim 1, wherein the humanized binding protein or antigen binding fragment further comprises: an immunoglobulin (Ig) constant heavy region comprising the amino acid sequence selected from the group consisting of SEQ ID NO: 2 and SEQ ID NO: 3; and an Ig constant light region comprising the amino acid sequence selected from the group consisting of SEQ ID NO: 4 and SEQ ID NO: 5.

13. The humanized binding protein or antigen binding fragment thereof of claim 1, wherein the binding protein or antigen binding fragment thereof is selected from the group consisting of an immunoglobulin molecule, an Fv, a disulfide linked Fv, a monoclonal antibody, an scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')2 fragment, a DVD-Ig™ protein, a bivalent fragment comprising two Fab fragments linked by a disulfide bridge at the hinge region; a Fd fragment consisting of the VH and CH1 domains; an Fv fragment consisting of the VL and VH domains of a single arm of an antibody, a dAb fragment, and a single chain antibody.

14. A crystallized binding protein comprising the binding protein or antigen binding fragment thereof of claim 1, wherein the binding protein or antigen binding fragment thereof is in the form of a crystal.

15. The crystallized binding protein of claim 14, wherein the crystal is a carrier-free pharmaceutical controlled release crystal.

16. The crystallized binding protein of claim 14, wherein the binding protein or antigen binding fragment thereof has a greater half life in vivo than the soluble counterpart of the binding protein or antigen binding fragment thereof.

17. A composition for the release of a TNF-α binding protein comprising: (a) a formulation, wherein the formulation comprises the binding protein or antigen binding fragment thereof of claim 1 or 14, and an ingredient; and (b) at least one polymeric carrier.

18. The composition of claim 17, wherein the ingredient is selected from the group consisting of albumin, sucrose, trehalose, lactitol, gelatin, hydroxypropyl-β-cyclodextrin, methoxypolyethylene glycol, and polyethylene glycol.

19. The composition of claim 17, wherein the polymeric carrier is a polymer selected from the group consisting of poly acrylic acid, poly cyanoacrylate, a poly amino acid, a poly anhydride, a poly depsipeptide, a poly ester, poly lactic acid, poly lactic-co-glycolic acid, poly b-hydroxybutryate, poly caprolactone, poly dioxanone, poly ethylene glycol, poly hydroxypropyl methacrylamide, poly organophosphazene, poly ortho esters, poly vinyl alcohol, poly vinylpyrrolidone, maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, and blends and copolymers thereof.

20. A tumor necrosis factor-alpha (TNF-α) binding protein construct comprising the humanized binding protein or antigen binding fragment thereof of claim 1, and a linker or an immunoglobulin constant domain.

21. The TNF-α binding protein construct of claim 20, wherein the binding protein or antigen binding fragment thereof is glycosylated.

22. The TNF-α binding protein construct of claim 20, wherein the binding protein construct is a crystallized TNF-α binding protein construct.

23. The TNF-α binding protein construct of claim 22, wherein the crystallized TNF-α binding protein construct is a carrier-free pharmaceutical controlled release crystallized TNF-α binding protein construct.

24. The TNF-α binding protein construct of claim 20, wherein the binding protein construct has a greater half life in vivo than the soluble counterpart of the binding protein construct.

25. A tumor necrosis factor-alpha (TNF-α) binding protein conjugate comprising the TNF-α binding protein construct of claim 20, and an agent selected from the group consisting of immunoadhesion molecule, an imaging agent, a therapeutic agent, or a cytotoxic agent.

26. The TNF-α binding protein conjugate of claim 25, wherein the imaging agent is a radiolabel, an enzyme, a fluorescent label, a luminescent label, a bioluminescent label, a magnetic label, or biotin.

27. The TNF-α binding protein conjugate of claim 26, wherein the radiolabel is selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$.

28. The TNF-α binding protein conjugate of claim 25, wherein the therapeutic agent or cytotoxic agent is selected from the group consisting of an anti-metabolite, an alkylating agent, an antibiotic, a growth factor, a cytokine, an anti-angiogenic agent, an anti-mitotic agent, an anthracycline, a toxin, or an apoptotic agent.

29. A pharmaceutical composition comprising the binding protein or antigen binding fragment thereof of claim 1, and a pharmaceutically acceptable carrier.

30. The pharmaceutical composition of claim 29, wherein the pharmaceutically acceptable carrier functions as an adjuvant.

31. The pharmaceutical composition of claim 30, wherein the adjuvant is hyaluronidase.

32. The pharmaceutical composition of claim 29, wherein the composition further comprises at least one additional agent for treating a disorder in which TNF-α activity is detrimental.

33. The pharmaceutical composition of claim 32, wherein the additional agent is selected from the group consisting of a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof, methotrexate, cyclosporine, rapamycin, FK506, a detectable label, a detectable reporter, a TNF-α antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive agent, a growth hormone, a hormone replacement drug, a radiopharmaceutical, an antidepressant, an antipsychotic, a stimulant, an asthma medication, a beta agonist, an inhaled steroid, an oral steroid, an epinephrine or analog thereof, a cytokine, and a cytokine antagonist.

* * * * *

SEQUENCE LISTING

```
<160> NUMBER OF SEQ ID NOS: 36

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Asp Arg
```

```
                    20                  25                  30
Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

-continued

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 6
<211> LENGTH: 31
<212> TYPE: PRT
<213> ORGANISM: Homo sapiens

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

<210> SEQ ID NO 7
<211> LENGTH: 14
<212> TYPE: PRT
<213> ORGANISM: Homo sapiens

<400> SEQUENCE: 7

Trp Ile Arg Gln Pro Pro Gly Lys Gly Leu Glu Trp Ile Gly
1               5                   10

<210> SEQ ID NO 8
<211> LENGTH: 32
<212> TYPE: PRT
<213> ORGANISM: Homo sapiens

<400> SEQUENCE: 8

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 9
<211> LENGTH: 31
<212> TYPE: PRT
<213> ORGANISM: Homo sapiens

<400> SEQUENCE: 9

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser
            20                  25                  30

<210> SEQ ID NO 10
<211> LENGTH: 14
<212> TYPE: PRT
<213> ORGANISM: Homo sapiens

<400> SEQUENCE: 10

Trp Val Arg Gln Ala Pro Gly Lys Gly Leu Glu Trp Val Ser
1               5                   10

<210> SEQ ID NO 11
<211> LENGTH: 32
<212> TYPE: PRT
<213> ORGANISM: Homo sapiens

<400> SEQUENCE: 11

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 12
<211> LENGTH: 11
<212> TYPE: PRT
<213> ORGANISM: Homo sapiens

<400> SEQUENCE: 12

Trp Gly Gln Gly Thr Leu Val Thr Val Ser Ser
1               5                   10

```
<210> SEQ ID NO 13
<211> LENGTH: 11
<212> TYPE: PRT
<213> ORGANISM: Homo sapiens

<400> SEQUENCE: 13

Trp Gly Arg Gly Thr Leu Val Thr Val Ser Ser
1               5                   10

<210> SEQ ID NO 14
<211> LENGTH: 11
<212> TYPE: PRT
<213> ORGANISM: Homo sapiens

<400> SEQUENCE: 14

Trp Gly Gln Gly Thr Thr Val Thr Val Ser Ser
1               5                   10

<210> SEQ ID NO 15
<211> LENGTH: 23
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Homo sapiens

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Homo sapiens

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 23
<212> TYPE: PRT
<213> ORGANISM: Homo sapiens

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 19
<211> LENGTH: 15
<212> TYPE: PRT
<213> ORGANISM: Homo sapiens
```

<400> SEQUENCE: 19

Trp Tyr Gln Gln Lys Pro Gly Gln Ala Pro Arg Leu Leu Ile Tyr
1               5                   10                  15

<210> SEQ ID NO 20
<211> LENGTH: 32
<212> TYPE: PRT
<213> ORGANISM: Homo sapiens

<400> SEQUENCE: 20

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 21
<211> LENGTH: 11
<212> TYPE: PRT
<213> ORGANISM: Homo sapiens

<400> SEQUENCE: 21

Phe Gly Gln Gly Thr Lys Leu Glu Ile Lys Arg
1               5                   10

<210> SEQ ID NO 22
<211> LENGTH: 117
<212> TYPE: PRT
<213> ORGANISM: Mus sp.

<400> SEQUENCE: 22

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asp Ser Thr Leu Lys
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Asp Asp Thr Ala Arg Tyr Tyr Cys Ala
                85                  90                  95

Arg Glu Trp His His Gly Pro Val Ala Tyr Trp Gly Gln Gly Thr Leu
            100                 105                 110

Val Thr Val Ser Ala
        115

<210> SEQ ID NO 23
<211> LENGTH: 108
<212> TYPE: PRT
<213> ORGANISM: Mus sp.

<400> SEQUENCE: 23

Asp Ile Val Met Thr Gln Ser His Lys Phe Met Ser Thr Thr Val Gly
1               5                   10                  15

Asp Arg Val Ser Ile Thr Cys Lys Ala Ser Gln Ala Val Ser Ala
            20                  25                  30

Val Ala Trp Tyr Gln Gln Lys Pro Gly Gln Ser Pro Lys Leu Leu Ile
        35                  40                  45

```
Tyr Trp Ala Ser Thr Arg His Thr Gly Val Pro Asp Arg Phe Thr Gly
        50                  55                  60

Ser Gly Ser Val Thr Asp Phe Thr Leu Thr Ile His Asn Leu Gln Ala
65                  70                  75                  80

Glu Asp Leu Ala Leu Tyr Tyr Cys Gln Gln His Tyr Ser Thr Pro Phe
                85                  90                  95

Thr Phe Gly Ser Gly Thr Lys Leu Glu Ile Lys Arg
                100                 105

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
                20                  25                  30

Gly Val Asn Trp Ile Arg Gln Pro Pro Gly Lys Gly Leu Glu Trp Ile
            35                  40                  45

Gly Met Ile Trp Gly Asp Gly Ser Thr Asp Tyr Asp Ser Thr Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Trp His His Gly Pro Val Ala Tyr Trp Cys Gln Gly Thr Leu
                100                 105                 110

Val Thr Val Ser Ser
        115

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Asp Tyr
                20                  25                  30

Gly Val Asn Trp Val Arg Gln Ala Pro Gly Lys Gly Leu Glu Trp Val
            35                  40                  45

Ser Met Ile Trp Gly Asp Gly Ser Thr Asp Tyr Asp Ser Thr Leu Lys
        50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Trp His His Gly Pro Val Ala Tyr Trp Gly Gln Gly Thr Leu
                100                 105                 110
```

```
Val Thr Val Ser Ser
         115

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ala Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ala Val Ser Ser Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
            20                  25                  30

Gly Val Asn Trp Ile Arg Gln Pro Pro Gly Lys Gly Leu Glu Trp Ile
            35                  40                  45

Gly Met Ile Trp Gly Asp Gly Ser Thr Asp Tyr Asp Ser Thr Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Trp His His Gly Pro Val Ala Tyr Trp Gly Gln Gly Thr Leu
            100                 105                 110

Val Thr Val Ser Ser
            115

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Asn Trp Val Arg Gln Pro Pro Gly Lys Gly Leu Glu Trp Leu
            35                  40                  45

Gly Met Ile Trp Gly Asp Gly Ser Thr Asp Tyr Asp Ser Thr Leu Lys
        50                  55                  60

Ser Arg Leu Thr Ile Ser Lys Asp Asn Ser Lys Ser Gln Ile Ser Leu
65                  70                  75                  80

Lys Leu Ser Ser Val Thr Ala Ala Asp Thr Ala Val Tyr Tyr Cys Ala
                85                  90                  95

Arg Glu Trp His His Gly Pro Val Ala Tyr Trp Gly Gln Gly Thr Leu
            100                 105                 110

Val Thr Val Ser Ser
            115

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Asn Trp Ile Arg Gln Pro Pro Gly Lys Gly Leu Glu Trp Ile
            35                  40                  45

```
Gly Met Ile Trp Gly Asp Gly Ser Thr Asp Tyr Asp Ser Thr Leu Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Trp His His Gly Pro Val Ala Tyr Trp Gly Gln Gly Thr Leu
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Val Asn Trp Val Arg Gln Ala Pro Gly Lys Gly Leu Glu Trp Val
        35                  40                  45

Ser Met Ile Trp Gly Asp Gly Ser Thr Asp Tyr Asp Ser Thr Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Trp His His Gly Pro Val Ala Tyr Trp Gly Gln Gly Thr Leu
            100                 105                 110

Val Thr Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Asp Tyr
            20                  25                  30

Gly Val Asn Trp Val Arg Gln Ala Pro Gly Lys Gly Leu Glu Trp Leu
        35                  40                  45

Gly Met Ile Trp Gly Asp Gly Ser Thr Asp Tyr Asp Ser Thr Leu Lys
    50                  55                  60

Ser Arg Leu Thr Ile Ser Lys Asp Asn Ser Lys Ser Thr Ile Tyr Leu
65                  70                  75                  80

Gln Met Asn Ser Leu Arg Ala Glu Asp Thr Ala Val Tyr Tyr Cys Ala
                85                  90                  95
```

```
Arg Glu Trp His His Gly Pro Val Ala Tyr Trp Gly Gln Gly Thr Leu
            100                 105                 110

Val Thr Val Ser Ser
            115

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asp Tyr
            20                  25                  30

Gly Val Asn Trp Val Arg Gln Ala Pro Gly Lys Gly Leu Glu Trp Val
        35                  40                  45

Ser Met Ile Trp Gly Asp Gly Ser Thr Asp Tyr Asp Ser Thr Leu Lys
50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Trp His His Gly Pro Val Ala Tyr Trp Gly Gln Gly Thr Leu
            100                 105                 110

Val Thr Val Ser Ser
            115

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ala Val Ser Ser Ala
            20                  25                  30

Val Ala Trp Tyr Gln Gln Lys Pro Gly Lys Ser Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Phe
            85                  90                  95

Thr Phe Gly Gln Gly Thr Lys Leu Glu Ile Lys
            100                 105

<210> SEQ ID NO 35
<211> LENGTH: 107
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 35

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Ala Val Ser Ser Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
                100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Ala Val Ser Ser Ala
            20                  25                  30

Val Ala Trp Tyr Gln Gln Lys Pro Gly Gln Ser Pro Arg Leu Leu Ile
        35                  40                  45

Tyr Trp Ala Ser Thr Arg His Thr Gly Val Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
                100                 105
```